(12) United States Patent
Kleinschek et al.

(10) Patent No.: US 11,786,517 B2
(45) Date of Patent: *Oct. 17, 2023

(54) METHODS OF TREATMENT USING A JAK INHIBITOR COMPOUND

(71) Applicant: THERAVANCE BIOPHARMA R&D IP, LLC, South San Francisco, CA (US)

(72) Inventors: Melanie A. Kleinschek, San Francisco, CA (US); Glenn D. Crater, Raleigh, NC (US)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 191 days.

This patent is subject to a terminal disclaimer.

(21) Appl. No.: 17/449,136

(22) Filed: Sep. 28, 2021

(65) Prior Publication Data
US 2022/0008403 A1 Jan. 13, 2022

Related U.S. Application Data

(60) Continuation of application No. 16/718,543, filed on Dec. 18, 2019, now Pat. No. 11,160,800, which is a division of application No. 16/525,859, filed on Jul. 30, 2019, now Pat. No. 10,548,886, which is a division of application No. 15/966,438, filed on Apr. 30, 2018, now Pat. No. 10,406,148.

(60) Provisional application No. 62/492,568, filed on May 1, 2017.

(51) Int. Cl.
| | |
|---|---|
| A61K 31/4545 | (2006.01) |
| A61P 27/02 | (2006.01) |
| A61K 9/00 | (2006.01) |
| A61P 11/00 | (2006.01) |

(52) U.S. Cl.
CPC .......... *A61K 31/4545* (2013.01); *A61K 9/008* (2013.01); *A61K 9/0019* (2013.01); *A61K 9/0048* (2013.01); *A61K 9/0075* (2013.01); *A61K 9/0078* (2013.01); *A61P 11/00* (2018.01); *A61P 27/02* (2018.01)

(58) Field of Classification Search
CPC .................................................. A61K 31/4545
See application file for complete search history.

(56) References Cited

U.S. PATENT DOCUMENTS

| | | | |
|---|---|---|---|
| 6,534,524 B1 | 3/2003 | Kania et al. | |
| 6,884,890 B2 | 4/2005 | Kania et al. | |
| 7,884,109 B2 | 2/2011 | Ohlmeyer et al. | |
| 8,193,197 B2 | 6/2012 | Hui | |
| 8,450,340 B2 | 5/2013 | Hood et al. | |
| 8,575,336 B2 | 11/2013 | Coe et al. | |
| 8,609,687 B2 | 12/2013 | Zhu | |
| 8,648,069 B2 | 2/2014 | Akritopoulou-Zanze | |
| 8,895,544 B2 | 11/2014 | Coe et al. | |
| 10,100,049 B2 | 10/2018 | Fatheree et al. | |
| 10,183,942 B2 | 1/2019 | Benjamin et al. | |
| 10,196,393 B2 | 2/2019 | Fatheree et al. | |
| 10,196,418 B2 | 2/2019 | Fatheree et al. | |
| 10,208,040 B2 | 2/2019 | Fatheree et al. | |
| 10,251,874 B2 | 4/2019 | Dabros et al. | |
| 10,392,386 B2 | 8/2019 | Fatheree et al. | |
| 10,406,148 B2* | 9/2019 | Kleinschek | A61K 9/0019 |
| 10,493,077 B2 | 12/2019 | Fatheree et al. | |
| 10,519,153 B2 | 12/2019 | Fatheree et al. | |
| 10,526,330 B2 | 1/2020 | Fatheree et al. | |
| 10,548,886 B2* | 2/2020 | Kleinschek | A61K 9/0078 |
| 10,913,740 B2 | 2/2021 | Fatheree et al. | |
| 2005/0090529 A1 | 4/2005 | McAlpine et al. | |
| 2015/0158864 A1 | 6/2015 | Thorarensen et al. | |
| 2015/0329542 A1 | 11/2015 | Coe et al. | |
| 2016/0289196 A1 | 10/2016 | Choi et al. | |
| 2018/0311255 A1 | 11/2018 | Fatheree et al. | |
| 2019/0106420 A1 | 4/2019 | Fatheree et al. | |
| 2019/0119275 A1 | 4/2019 | Fatheree et al. | |

(Continued)

FOREIGN PATENT DOCUMENTS

| | | |
|---|---|---|
| JP | 2010111624 A | 5/2010 |
| WO | 2005009389 A2 | 2/2005 |

(Continued)

OTHER PUBLICATIONS

Mark Abelson et al., "Sorting out the stats from the Jaks," Review of Ophthamology, p. 84-88 (2013).

(Continued)

*Primary Examiner* — Svetlana M Ivanova
(74) *Attorney, Agent, or Firm* — SHEPPARD MULLIN RICHTER & HAMPTON LLP

(57) ABSTRACT

The invention relates to methods of treating ocular diseases and certain respiratory diseases using the compound 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol

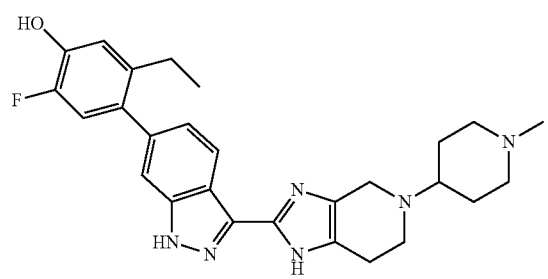

or a pharmaceutically-acceptable salt thereof.

20 Claims, No Drawings

(56) References Cited

U.S. PATENT DOCUMENTS

| | | | |
|---|---|---|---|
| 2019/0127371 A1 | 5/2019 | Fatheree et al. |
| 2019/0350916 A1 | 11/2019 | Kleinschek et al. |
| 2020/0087303 A1 | 3/2020 | Fatheree et al. |
| 2020/0121669 A1 | 4/2020 | Thalladi et al. |

FOREIGN PATENT DOCUMENTS

| | | | |
|---|---|---|---|
| WO | 2010039825 A2 | 4/2010 |
| WO | 2010114971 A1 | 10/2010 |
| WO | 2011017178 A1 | 2/2011 |
| WO | 2011076419 A1 | 6/2011 |
| WO | 2012121764 A1 | 9/2012 |
| WO | 2013014567 A1 | 1/2013 |
| WO | 2013151708 A1 | 10/2013 |
| WO | 2015061665 A1 | 4/2015 |
| WO | 2015173683 A1 | 11/2015 |
| WO | 2016026078 A1 | 2/2016 |
| WO | 2017077283 A1 | 5/2017 |
| WO | 2017077288 A1 | 5/2017 |

OTHER PUBLICATIONS

Thalladi et al., U.S. Appl. No. 15/966,438, filed Apr. 30, 2018.
Kleinschek et al., U.S. Appl. No. 16/525,859, filed Jul. 30, 2019.
Thalladi et al., U.S. Appl. No. 16/718,543, filed Dec. 18, 2019.
Abcouwer, "Angiogenic factors and cytokines in diabetic retinopathy", J Clin Cell Immunol, Supplement 1: 1-12 (2013).
Bao et al., "The involvement of the JAK-STAT signaling pathway in chronic inflammatory skin disease atopic dermatitis", JAK-STAT, 2(3): e24137-1-e24137-8 (2013).
Berastegui et al., "BALF cytokines in different phenotypes of chronic lung allograft dysfunction in lung transplant patients", Clinical Transplantation, 31: e12898 (2017).
Coghill et al., "Effector CD4+ T cells, the cytokines they generate, and GVHD: something old and something new", Blood, 117(12): 3268-3276 (Mar. 24, 2011).
The International Search Report and the Written Opinion for PCT/US2018/030140 dated Jul. 4, 2018.
Cottin, "Eosinophilic lung diseases", Clin Chest Med, 37: 535-556 (2016).
Craiglow et al., "Tofacitinib citrate for the treatment of vitiligo: A pathogenesis-directed therapy", JAMA Dermatology, 151: 1110-1112 (2015).
De Nitto et al., "Involvement of interleukin-15 and interleukin-21, two gamma-chain-related cytokines, in celiac disease", World J Gastroenterol, 15(37): 4609-4614 (Oct. 7, 2009).
Deobhakta et al., "Inflammation in retinal vein occlusion", International Journal of Inflammation, vol. 2013, 6 pages (2013).
El-Hashemite et al., "Interferon-gamma-Jak-Stat signaling in pulmonary lymphangioleiomyomatosis and renal angiomyolipoma", Am J Respir Cell Mol Biol, 33: 227-230 (2005).
El-Hashemite et al., "Perturbed IFN-gamma-Jak-signal transducers and activators of transcription signaling in tuberous sclerosis mouse models: Synergistic effects of rapamycin-IFN-gamma treatment", Cancer Research, 64: 3436-3443 (May 15, 2004).
Fang et al., "Interleukin-6 -572C/G polymorphism is associated with serum interleukin-6 levels and risk of idiopathic pulmonary arterial hypertension", Journal of the American Society of Hypertension, 11(3): 171-177 (2017).
Feliciani et al., "A TH2-like cytokine response is involved in bullous pemphigoid. The role of IL-4 and IL-5 in the pathogenesis of the disease", International Journal of Immunopathology and Pharmacology, 12(2): 55-61 (1999).
Fenwick et al., "Effect of JAK inhibitors on release of CXCL9, CXCL10 and CXCL11 from human airway epithelial cells", PLOS One, 10(6): e0128757 (2015).
Foloppe et al., "Identification of a buried pocket for potent and selective inhibition of Chk1: Prediction and verification", Bioorganic & Medicinal Chemistry, 14: 1792-1804 (2006).
Funatsu et al., "Association of vitreous inflammatory factors with diabetic macular edema", Ophthalmology, 116: 73-79 (2009).
Gauthier et al., "Update on chronic lung allograft dysfunction", Curr Transplant Rep, 3(3): 185-191 (Sep. 2016).
Horai et al, "Cytokines in autoimmune uveitis", Journal of Interferon & Cytokine Research, 31(10): 733-744 (2011).
Huang et al., "Glycoprotein 130 inhibitor ameliorates monocrotalline-induced pulmonary hypertension in rats", Canadian Journal of Cardiology, 32: 1356.e1-1356.e10 (2016).
Jones et al., "Design and synthesis of a Pan-Janus kinase inhibitor clinical candidate (PF-06263276) suitable for inhaled and topical delivery for the treatment of inflammatory diseases of the lungs and skin", J. Med. Chem., 60: 767-786 (2017).
Knickelbein et al., "Inflammatory mechanisms of age-related macular degeneration", International Ophthalmology Clinics, 55(3): 63-78 (2015).
Kudlacz et al., "The JAK-3 inhibitor CP-690550 is a potent anti-inflammatory agent in a murine model of pulmonary eosinophilia", European Journal of Pharmacology, 582: 154-161 (2008).
Kumawat et al., "Microscopic colitis patients demonstrate a mixed Th17/Tc17 and Th1/Tc1 mucosal cytokine profile", Molecular Immunology, 55: 355-364 (2013).
Malaviya et al., "Janus Kinase-3 dependent inflammatory responses in allergic asthma", International Immunopharmacology, 10: 829-836 (2010).
Matsunaga et al., "Effects of a Janus kinase inhibitor, pyridone 6, on airway responses in a murine model of asthma", Biochemical and Biophysical Research Communications, 404: 261-267 (2011).
McBride et al., "Design and structure-activity relationship of 3-benzimidazol-2-yl-1H-indazoles as inhibitors of receptor tyrosine kinases", Bioorganic & Medicinal Chemistry Letters, 16: 3595-3599 (2006).
McBride et al., "3-Benzimidazol-2-yl-1H-indazoles as potent c-ABL inhibitors", Bioorganic & Medicinal Chemistry Letters, 16: 3789-3792 (2006).
Netchiporouk et al., "Deregulation in STAT signaling is important for cutaneous T-cell lymphoma (CTCL) pathogenesis and cancer progression", Cell Cycle, 13(21): 3331-3335 (Nov. 1, 2014).
Okiyama et al., "Reversal of CD8 T-cell-mediated mucocutaneous graft-versus-host-like disease by the JAK inhibitor tofacitinib", Journal of Investigative Dermatology, 134: 992-1000 (2014).
Owen et al., "Soluble mediators of diabetic macular edema: The diagnostic role of aqueous VEGF and cytokine levels in diabetic macular edema", Curr Diab Rep, 13(4): 476-480 (Aug. 2013).
Reimund et al., "Mucosal inflammatory cytokine production by intestinal biopsies in patients with ulcerative colitis and Crohn's disease", Journal of Clinical Immunology, 16(3): 144-150 (1996).
Shchuko et al., "Intraocular cytokines in retinal vein occlusion and its relation to the efficiency of anti-vascular endothelial growth factor therapy", Indian Journal of Ophthalmology, 63: 905-911 (2015).
Shino et al., "The prognostic importance of CXCR3 chemokine during organizing pneumonia on the risk of chronic lung allograft dysfunction after lung transplantation", PLOS One, 12(7): e0180281 (2017).
Simov et al., "Structure-based design and development of (benz)imidazole pyridones as JAK1-selective kinase inhibitors", Bioorganic & Medicinal Chemistry Letters, 26: 1803-1808 (2016).
Sohn et al., "Changes in aqueous concentrations of various cytokines after intravitreal triamcinolone versus bevacizumab for diabetic macular edema", Ophthalmology, 152: 686-694 (2011).
Sonkoly et al., "IL-31: A new link between T cells and pruritus in atopic skin inflammation", J Allergy Clin Immunol, 117(2): 411-417 (2006).
Stallmach et al., "Cytokine/chemokine transcript profiles reflect mucosal inflammation in Crohn's disease", Int J Colorectal Dis, 19: 308-315 (2004).
Stevenson et al., "Dry eye disease", Arch Ophthalmol, 130(1): 90-100 (Jan. 2012).
Tanaka et al., "New insight into mechanisms of pruritus from molecular studies on familial primary localized cutaneous amyloidosis", British Journal of Dermatology, 161: 1217-1224 (2009).

(56) References Cited

OTHER PUBLICATIONS

Trujillo et al., "2-(6-Phenyl-1H-indazol-3-yl)-1H-benzo[d]imidazoles: Design and synthesis of a potent and isoform selective PKC-zeta inhibitor", Bioorganic & Medicinal Chemistry Letters, 19: 908-911 (2009).

Vincenti et al., "Randomized phase 2b trial of tofacitinib (CP-690,550) in de novo kidney transplant patients: Efficacy, renal function and safety at 1 year", American Journal of Transplantation, 12: 2446-2456 (2012).

Weinbrand-Goichberg et al., "Eosinophilic esophagitis: an immune-mediated esophageal disease", Immunol Res, 56: 249-260 (2013).

Welz-Kubiak et al., "IL-31 is overexpressed in lichen planus but its level does not correlate with pruritus severity", Journal of Immunology Research, Article 854747, 6 pages (2015).

Woywodt et al., "Mucosal cytokine expression, cellular markers and adhesion molecules in inflammatory bowel disease", European Journal of Gastroenterology & Hepatology, 11: 267-276 (1999).

Xing et al., "Alopecia areata is driven by cytotoxic T lymphocytes and is reversed by JAK inhibition", Nature Medicine, 20(9): 1043-1049 (Sep. 2014).

Yamamoto et al., "Mucosal inflammation in the terminal ileum of ulcerative colitis patients: Endoscopic findings and cytokine profiles", Digestive and Liver Disease, 40: 253-259 (2008).

Yan et al., "Discovery of 3-(5'-Substituted)-benzimidazol-5-(1-(3,5-dichloropyridin-4-yl)ethoxy)-1H-indazoles as potent fibroblast growth factor receptor inhibitors: Design, synthesis, and biological evaluation", J. Med. Chem., 59: 6690-6708 (2016).

Yano et al., "Ipilimumab augments antitumor activity of bispecific antibody-armed T cells", Journal of Translational Medicine, 12: 191 (2014).

Zeiser et al., "Ruxolitinib in corticosteroid-refractory graft-versus-host disease after allogeneic stem cell transplantation: a multi-center survey", Leukemia, 29(10): 2062-2068 (Oct. 2015).

Zhou et al., "Cytokines and Behcet's Disease", Autoimmunity Reviews, 11: 699-704 (2012).

Lu et al., "Role of a janus kinase 2-dependent signaling pathway in platelet activation", Thromb. Res., 133(6): 1088-1096 (2014).

* cited by examiner

METHODS OF TREATMENT USING A JAK INHIBITOR COMPOUND

CROSS-REFERENCE TO RELATED APPLICATIONS

This application is a continuation application of U.S. Ser. No. 16/718,543, filed on Dec. 18, 2019, now allowed, which is a divisional application of U.S. Ser. No. 16/525,859, filed on Jul. 30, 2019, now U.S. Pat. No. 10,548,886, which is a divisional application of U.S. Ser. No. 15/966,438, filed on Apr. 30, 2018, now U.S. Pat. No. 10,406,148, which application claims the benefit of U.S. Provisional Application No. 62/492,568, filed on May 1, 2017, the disclosures of which are incorporated herein by reference in their entirety.

BACKGROUND OF THE INVENTION

Field of the Invention

The present invention is directed to methods for treating ocular and certain respiratory diseases using a particular JAK inhibitor compound or a pharmaceutically-acceptable salt thereof.

State of the Art

Cytokines are intercellular signaling molecules which include chemokines, interferons, interleukins, lymphokines, and tumour necrosis factor. Cytokines are critical for normal cell growth and immunoregulation but also drive immune-mediated diseases and contribute to the growth of malignant cells. Elevated levels of many cytokines have been implicated in the pathology of a large number of diseases or conditions, particularly those diseases characterized by inflammation. Many of the cytokines implicated in disease act through signaling pathways dependent upon the Janus family of tyrosine kinases (JAKs), which signal through the Signal Transducer and Activator of Transcription (STAT) family of transcription factors.

The JAK family comprises four members, JAK1, JAK2, JAK3, and tyrosine kinase 2 (TYK2). Binding of cytokine to a JAK-dependent cytokine receptor induces receptor dimerization which results in phosphorylation of tyrosine residues on the JAK kinase, effecting JAK activation. Phosphorylated JAKs, in turn, bind and phosphorylate various STAT proteins which dimerize, internalize in the cell nucleus and directly modulate gene transcription, leading, among other effects, to the downstream effects associated with inflammatory disease. The JAKs usually associate with cytokine receptors in pairs as homodimers or heterodimers. Specific cytokines are associated with specific JAK pairings. Each of the four members of the JAK family is implicated in the signaling of at least one of the cytokines associated with inflammation.

Inflammation plays a prominent role in many ocular diseases, including uveitis, diabetic retinopathy, diabetic macular edema, dry eye disease, age-related macular degeneration, and atopic keratoconjunctivitis. Uveitis encompasses multiple intraocular inflammatory conditions and is often autoimmune, arising without a known infectious trigger. The condition is estimated to affect about 2 million patients in the US. In some patients, the chronic inflammation associated with uveitis leads to tissue destruction, and it is the fifth leading cause of blindness in the US. Cytokines elevated in uveitis patients' eyes that signal through the JAK-STAT pathway include IL-2, IL-4, IL-5, IL-6, IL-10, IL-23, and IFN-γ. (Horai and Caspi, *J Interferon Cytokine Res*, 2011, 31, 733-744; Ooi et al, *Clinical Medicine and Research*, 2006, 4, 294-309). Existing therapies for uveitis are often suboptimal, and many patients are poorly controlled. Steroids, while often effective, are associated with cataracts and increased intraocular pressure/glaucoma.

Diabetic retinopathy (DR) is caused by damage to the blood vessels in the retina. It is the most common cause of vision loss among people with diabetes. Angiogenic as well as inflammatory pathways play an important role in the disease. Often, DR will progress to diabetic macular edema (DME), the most frequent cause of visual loss in patients with diabetes. The condition is estimated to affect about 1.5 million patients in the US alone, of whom about 20% have disease affecting both eyes. Cytokines which signal through the JAK-STAT pathway, such as IL-6, as well as other cytokines, such as IP-10 and MCP-1 (alternatively termed CCL2), whose production is driven in part by JAK-STAT pathway signaling, are believed to play a role in the inflammation associated with DR/DME (Abcouwer, *J Clin Cell Immunol*, 2013, Suppl 1, 1-12; Sohn et al., *American Journal of Opthalmology*, 2011, 152, 686-694; Owen and Hartnett, *Curr Diab Rep*, 2013, 13, 476-480; Cheung et al, *Molecular Vision*, 2012, 18, 830-837; Dong et al, *Molecular Vision*, 2013, 19, 1734-1746; Funatsu et al, *Ophthalmology*, 2009, 116, 73-79). The existing therapies for DME are suboptimal: intravitreal anti-VEGF treatments are only effective in a fraction of patients and steroids are associated with cataracts and increased intraocular pressure.

Dry eye disease (DED) is a multifactorial disorder that affects approximately 5 million patients in the US. Ocular surface inflammation is believed to play an important role in the development and propagation of this disease. Elevated levels of cytokines such as IL-1, IL-2, IL-4, IL-5, IL-6, and IFN-γ have been noted in the ocular fluids of patients with DED. (Stevenson et al, *Arch Ophthalmol*, 2012, 130, 90-100), and the levels often correlated with disease severity. Age-related macular degeneration and atopic keratoconjunctivitis are also thought to be associated with JAK-dependent cytokines.

Given the number of cytokines elevated in inflammatory diseases and that each cytokine is associated with a particular JAK pairing, it would be desirable to provide a chemical inhibitor with pan-activity against all members of the JAK family for the treatment of ocular disease. However, the broad anti-inflammatory effect of such inhibitors could suppress normal immune cell function, potentially leading to increased risk of infection. It would be desirable, therefore, to provide an inhibitor that can be locally delivered to the site of action in the eye, thereby limiting the potential for adverse systemic immunosuppression.

Commonly assigned U.S. application Ser. No. 15/341,226, filed Nov. 2, 2016 discloses diamino compounds useful as JAK inhibitors. In particular, the compound 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol (compound 1)

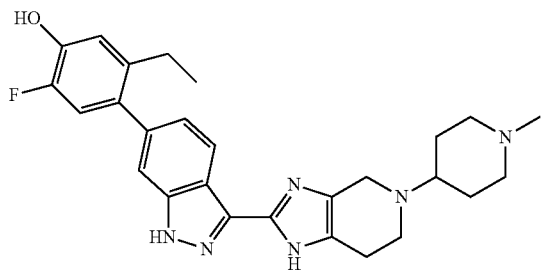 [SMILES: CCc1cc(O)c(F)cc1-c1ccc2c(-c3nc4c([nH]3)CCN(C3CCN(C)CC3)C4)n[nH]c2c1]

1 is specifically disclosed in the application as a potent pan-JAK inhibitor. This application discloses various uses of compound 1, in particular treatment of respiratory diseases including asthma, chronic obstructive pulmonary disease, cystic fibrosis, pneumonitis, interstitial lung diseases (including idiopathic pulmonary fibrosis), acute lung injury, acute respiratory distress syndrome, bronchitis, emphysema and bronchiolitis obliterans. However, this application does not disclose the use of compound 1 for the treatment of ocular disease.

SUMMARY OF THE INVENTION

The present invention relates to methods of treating ocular diseases or symptoms thereof using the JAK inhibitor 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol or a pharmaceutically-acceptable salt thereof.

In one aspect, the invention provides a method of treating an ocular disease in a human patient, the method comprising administering to the eye of the patient, the compound 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol of formula

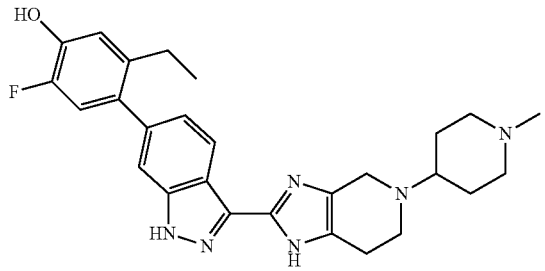

1 hereinafter compound 1, or a pharmaceutically-acceptable salt thereof.

In one aspect the ocular disease is uveitis, diabetic retinopathy, diabetic macular edema, dry eye disease, age-related macular degeneration, or atopic keratoconjunctivitis. In particular, the ocular disease is uveitis or diabetic macular edema.

In another aspect, the invention provides a pharmaceutical composition of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol (compound 1) or a pharmaceutically-acceptable salt thereof, wherein the pharmaceutical composition is suitable for administration directly to the eye of a patient.

The present invention further relates to methods of using compound 1 to treat certain specific respiratory diseases.

In one aspect, the invention provides a method of treating a respiratory disease in a mammal, the method comprising administering to the mammal a pharmaceutical composition comprising compound 1 or a pharmaceutically acceptable salt thereof, and a pharmaceutically-acceptable carrier, wherein the respiratory disease is a lung infection, a helminthic infection, pulmonary arterial hypertension, sarcoidosis, lymphangioleiomyomatosis, bronchiectasis, or an infiltrative pulmonary disease.

In yet another aspect, the invention provides a method of treating a respiratory disease in a mammal, the method comprising administering to the mammal a pharmaceutical composition comprising compound 1 or a pharmaceutically acceptable salt thereof, and a pharmaceutically-acceptable carrier, wherein the respiratory disease is drug-induced pneumonitis, fungal induced pneumonitis, allergic bronchopulmonary aspergillosis, hypersensitivity pneumonitis, eosinophilic granulomatosis with polyangiitis, idiopathic acute eosinophilic pneumonia, idiopathic chronic eosinophilic pneumonia, hypereosinophilic syndrome, Loffler syndrome, bronchiolitis obliterans organizing pneumonia, or immune-checkpoint-inhibitor induced pneumonitis.

DETAILED DESCRIPTION OF THE INVENTION

Chemical structures are named herein according to IUPAC conventions as implemented in ChemDraw software (PerkinElmer, Inc., Cambridge, Mass.).

Furthermore, the imidazo portion of the tetrahydroimidazopyridine moiety in the structure of the present compound exists in tautomeric forms. The compound could equivalently be represented as

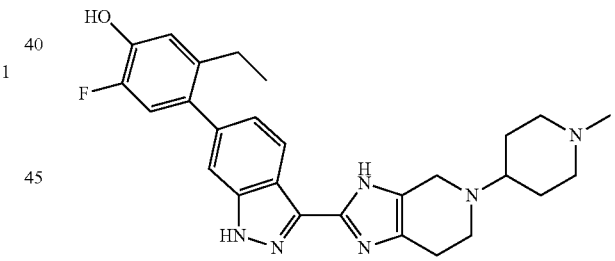

According to the IUPAC convention, these representations give rise to different numbering of the atoms of the imidazopyridine portion. Accordingly this structure is designated 5-ethyl-2-fluoro-4-(3-(5-(1-methylpiperidin-4-yl)-4,5,6,7-tetrahydro-3H-imidazo[4,5-c]pyridin-2-yl)-1H-indazol-6-yl)phenol. It will be understood that although structures are shown, or named, in a particular form, the invention also includes the tautomer thereof.

Definitions

When describing the present invention, the following terms have the following meanings unless otherwise indicated.

The singular terms "a," "an" and "the" include the corresponding plural terms unless the context of use clearly dictates otherwise.

The term "about" means ±5 percent of the specified value.

The term "therapeutically effective amount" means an amount sufficient to effect treatment when administered to a patient in need of treatment, e.g., the amount needed to obtain the desired therapeutic effect.

The term "treating" or "treatment" means preventing, ameliorating or suppressing the medical condition, disease or disorder being treated (e.g., a respiratory disease) in a patient (particularly a human); or alleviating the symptoms of the medical condition, disease or disorder.

The term "unit dosage form" or "unit doses" means a physically discrete unit suitable for dosing a patient, i.e., each unit containing a predetermined quantity of a therapeutic agent calculated to produce a therapeutic effect either alone or in combination with one or more additional units. Examples include capsules, tablets and the like.

All other terms used herein are intended to have their ordinary meaning as understood by persons having ordinary skill in the art to which they pertain.

The term "pharmaceutically-acceptable" means acceptable for administration to a patient (e.g., having acceptable safety for the specified usage).

The term "pharmaceutically-acceptable salt" means a salt prepared from an acid and a base (including zwitterions) that is acceptable for administration to a patient (e.g., a salt having acceptable safety for a given dosage regime).

Representative pharmaceutically acceptable salts include salts of acetic, ascorbic, benzenesulfonic, benzoic, camphorsulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, oxalic, pamoic, pantothenic, phosphoric, succinic, sulfuric, tartaric, p-toluenesulfonic and xinafoic acid, and the like.

The term "salt thereof" means a compound formed when the hydrogen of an acid is replaced by a cation, such as a metal cation or an organic cation and the like.

Compound 1

The present method invention employs 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol (compound 1)

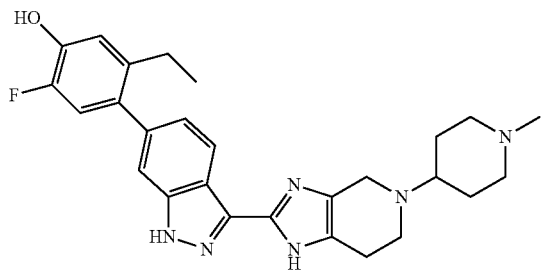

1 or a pharmaceutically-acceptable salt thereof.

Compound 1 may be prepared as described in U.S. application Ser. No. 15/341,226 or in the appended examples.

In one aspect of the invention, compound 1 is employed in the form of a crystalline freebase hydrate characterized by a powder X-ray diffraction (PXRD) pattern having significant diffraction peaks, among other peaks, at 2θ values of 6.20±0.20, 9.58±0.20, 17.53±0.20, 19.28±0.20, and 21.51±0.20. The preparation of the crystalline hydrate is also described in U.S. Ser. No. 15/341,226 and in the examples below.

Pharmaceutical Compositions

The present compound, 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol (1) and pharmaceutically-acceptable salts thereof is typically used in the form of a pharmaceutical composition or formulation. Such pharmaceutical compositions may advantageously be administered to a patient by any acceptable route of administration including, but not limited to, oral, inhalation, optical injection, topical (including transdermal), rectal, nasal, and parenteral modes of administration.

The pharmaceutical compositions utilized in the invention typically contain a therapeutically effective amount of compound 1. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount. When discussing compositions and uses, compound 1 may also be referred to herein as 'active agent'.

Typically, pharmaceutical compositions will contain from about 0.01 to about 95% by weight of the active agent; including, for example, from about 0.05 to about 30% by weight; and from about 0.1% to about 10% by weight of the active agent.

Any conventional carrier or excipient may be used in the pharmaceutical compositions utilized in the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this invention are commercially-available. By way of further illustration, conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution;

ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

In one aspect, the pharmaceutical composition is suitable for ocular injection. In this aspect, the compound may be formulated as a sterile aqueous suspension or solution. Useful excipients that may be included in such an aqueous formulation include polysorbate 80, carboxymethylcellulose, potassium chloride, calcium chloride, magnesium chloride, sodium acetate, sodium citrate, histidine, α-α-trehalose dihydrate, sucrose, polysorbate 20, hydroxypropyl-β-cyclodextrin, and sodium phosphate. Benzyl alcohol may serve as a preservative and sodium chloride may be included to adjust tonicity. In addition, hydrochloric acid and/or sodium hydroxide may be added to the solution for pH adjustment. Aqueous formulations for ocular injection may be prepared as preservative-free.

In another aspect, the pharmaceutical composition is suitable for inhaled administration. Pharmaceutical compositions for inhaled administration are typically in the form of an aerosol or a powder. Such compositions are generally administered using inhaler delivery devices, such as a dry powder inhaler (DPI), a metered-dose inhaler (MDI), a nebulizer inhaler, or a similar delivery device.

In a particular embodiment, the pharmaceutical composition is administered by inhalation using a dry powder inhaler. Such dry powder inhalers typically administer the pharmaceutical composition as a free-flowing powder that is dispersed in a patient's air-stream during inspiration. In order to achieve a free-flowing powder composition, the therapeutic agent is typically formulated with a suitable excipient such as lactose, starch, mannitol, dextrose, polylactic acid (PLA), polylactide-co-glycolide (PLGA) or combinations thereof. Typically, the therapeutic agent is micronized and combined with a suitable carrier to form a composition suitable for inhalation.

A representative pharmaceutical composition for use in a dry powder inhaler comprises lactose and the compound of the invention in micronized form. Such a dry powder composition can be made, for example, by combining dry milled lactose with the therapeutic agent and then dry blending the components. The composition is then typically loaded into a dry powder dispenser, or into inhalation cartridges or capsules for use with a dry powder delivery device.

Dry powder inhaler delivery devices suitable for administering therapeutic agents by inhalation are described in the art and examples of such devices are commercially available. For example, representative dry powder inhaler delivery devices or products include Aeolizer (Novartis); Airmax (IVAX); ClickHaler (Innovata Biomed); Diskhaler (GlaxoSmithKline); Diskus/Accuhaler (GlaxoSmithKline); Ellipta (GlaxoSmithKline); Easyhaler (Orion Pharma); Eclipse (Aventis); FlowCaps (Hovione); Handihaler (Boehringer Ingelheim); Pulvinal (Chiesi); Rotahaler (GlaxoSmithKline); SkyeHaler/Certihaler (SkyePharma); Twisthaler (Schering-Plough); Turbuhaler (AstraZeneca); Ultrahaler (Aventis); and the like.

In another particular embodiment, the pharmaceutical composition is administered by inhalation using a metered-dose inhaler. Such metered-dose inhalers typically discharge a measured amount of a therapeutic agent using a compressed propellant gas. Accordingly, pharmaceutical compositions administered using a metered-dose inhaler typically comprise a solution or suspension of the therapeutic agent in a liquefied propellant. Any suitable liquefied propellant may be employed including hydrofluoroalkanes (HFAs), such as 1,1,1,2-tetrafluoroethane (HFA 134a) and 1,1,1,2,3,3,3-heptafluoro-n-propane, (HFA 227); and chlorofluorocarbons, such as $CCl_3F$. In a particular embodiment, the propellant is hydrofluoroalkanes. In some embodiments, the hydrofluoroalkane formulation contains a co-solvent, such as ethanol or pentane, and/or a surfactant, such as sorbitan trioleate, oleic acid, lecithin, and glycerin.

A representative pharmaceutical composition for use in a metered-dose inhaler comprises from about 0.01% to about 5% by weight of the compound of the invention; from about 0% to about 20% by weight ethanol; and from about 0% to about 5% by weight surfactant; with the remainder being an HFA propellant. Such compositions are typically prepared by adding chilled or pressurized hydrofluoroalkane to a suitable container containing the therapeutic agent, ethanol (if present) and the surfactant (if present). To prepare a suspension, the therapeutic agent is micronized and then combined with the propellant. The composition is then loaded into an aerosol canister, which typically forms a portion of a metered-dose inhaler device.

Metered-dose inhaler devices suitable for administering therapeutic agents by inhalation are described in the art and examples of such devices are commercially available. For example, representative metered-dose inhaler devices or products include AeroBid Inhaler System (Forest Pharmaceuticals); Atrovent Inhalation Aerosol (Boehringer Ingelheim); Flovent (GlaxoSmithKline); Maxair Inhaler (3M); Proventil Inhaler (Schering); Serevent Inhalation Aerosol (GlaxoSmithKline); and the like.

In another particular aspect, the pharmaceutical composition is administered by inhalation using a nebulizer inhaler. Such nebulizer devices typically produce a stream of high velocity air that causes the pharmaceutical composition to spray as a mist that is carried into the patient's respiratory tract. Accordingly, when formulated for use in a nebulizer inhaler, the therapeutic agent can be dissolved in a suitable carrier to form a solution. Alternatively, the therapeutic agent can be micronized or nanomilled and combined with a suitable carrier to form a suspension.

A representative pharmaceutical composition for use in a nebulizer inhaler comprises a solution or suspension comprising from about 0.05 μg/mL to about 20 mg/mL of the compound of the invention and excipients compatible with nebulized formulations. In one embodiment, the solution has a pH of about 3 to about 8.

Nebulizer devices suitable for administering therapeutic agents by inhalation are described in the art and examples of such devices are commercially available. For example, representative nebulizer devices or products include the Respimat Softmist Inhaler (Boehringer Ingelheim); the AERx Pulmonary Delivery System (Aradigm Corp.); the PARI LC Plus Reusable Nebulizer (Pari GmbH); and the like.

In yet another aspect, the pharmaceutical compositions of the invention may alternatively be prepared in a dosage form intended for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form, the pharmaceutical compositions of the invention will typically comprise the active agent and one or more pharmaceutically-acceptable carriers, such as sodium citrate or dicalcium phosphate. Optionally or alternatively, such solid dosage forms may also comprise: fillers or extenders, binders, humectants, solution retarding agents, absorption accelerators, wetting agents, absorbents, lubricants, coloring agents, and buffering agents. Release agents, wetting agents, coating agents, sweetening, flavoring and perfuming agents, preservatives and antioxidants can also be present in the pharmaceutical compositions of the invention.

Alternative formulations may also include controlled release formulations, liquid dosage forms for oral administration, transdermal patches, and parenteral formulations. Conventional excipients and methods of preparation of such alternative formulations are described, for example, in the reference by Remington, supra.

The following non-limiting examples illustrate representative pharmaceutical compositions of the present invention.

Aqueous Formulation for Ocular Injection

Each mL of a sterile aqueous suspension includes from 5 mg to 50 mg of compound 1, sodium chloride for tonicity, 0.99% (w/v) benzyl alcohol as a preservative, 0.75% carboxymethylcellulose sodium, and 0.04% polysorbate. Sodium hydroxide or hydrochloric acid may be included to adjust pH to 5 to 7.5.

Aqueous Formulation for Ocular Injection

A sterile preservative-free aqueous suspension includes from 5 mg/mL to 50 mg/mL of compound 1 in 10 mM sodium phosphate, 40 mM sodium chloride, 0.03% polysorbate 20, and 5% sucrose.

Dry Powder Composition

Micronized compound 1 (1 g) is blended with milled lactose (25 g). This blended mixture is then loaded into individual blisters of a peelable blister pack in an amount sufficient to provide between about 0.1 mg to about 4 mg of the compound of formula I per dose. The contents of the blisters are administered using a dry powder inhaler.

Dry Powder Composition

Micronized compound 1 (1 g) is blended with milled lactose (20 g) to form a bulk composition having a weight ratio of compound to milled lactose of 1:20. The blended composition is packed into a dry powder inhalation device capable of delivering between about 0.1 mg to about 4 mg of the compound of formula I per dose.

Metered-Dose Inhaler Composition

Micronized compound 1 (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 µm. The micronized composition is then loaded into metered-dose inhaler cartridges containing pressurized 1,1,1,2-tetrafluoroethane in an amount sufficient to provide about 0.1 mg to about 4 mg of the compound of formula T per dose when administered by the metered dose inhaler.

Nebulizer Composition

Compound 1 (25 mg) is dissolved in a solution containing 1.5-2.5 equivalents of hydrochloric acid, followed by addition of sodium hydroxide to adjust the pH to 3.5 to 5.5 and 3% by weight of glycerol. The solution is stirred well until all the components are dissolved. The solution is administered using a nebulizer device that provides about 0.1 mg to about 4 mg of the compound of formula I per dose.

Utility

The present compound, 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol, (compound 1), has been shown to be a potent inhibitor of the JAK family of enzymes: JAK1, JAK2, JAK3, and TYK2.

Ocular Diseases

Many ocular diseases have been shown to be associated with elevations of proinflammatory cytokines that rely on the JAK-STAT pathway. Since the compound of the invention exhibits potent inhibition at all four JAK enzymes, it is expected to potently inhibit the signaling and pathogenic effects of numerous cytokines (such as IL-6, IL-2 and IFN-γ), that signal through JAK, as well as to prevent the increase in other cytokines (such as MCP-1 and IP-10), whose production is driven by JAK-STAT pathway signaling.

In particular, the present compound exhibited $pIC_{50}$ values of 6.7 or greater ($IC_{50}$ values of 200 nM or less) for inhibition of IL-2, IL-4, IL-6, and IFNγ signaling in the cellular assays described in Assays 3 to 7, including assays registering inhibition of the downstream effects of cytokine elevation.

The pharmacokinetic study of Assay 8 demonstrated sustained exposure in rabbit eyes after a single intravitreal injection and a concentration in plasma at least three orders of magnitude lower than that observed in vitreous tissue.

Furthermore, intravitreal dosing of the compound of the invention has demonstrated significant inhibition of IL-6 induced pSTAT3 in the rat retina/choroid tissue as well as significant inhibition of IFN-γ induced IP-10 in the rabbit vitreous as well as retina/choroid tissues.

It is expected that sustained ocular JAK inhibition in the absence of significant systemic levels will result in potent, local anti-inflammatory activity in the eye without systemically-driven adverse effects. The compound of the invention is expected to be beneficial in a number of ocular diseases that include, but are not limited to, uveitis, diabetic retinopathy, diabetic macular edema, dry eye disease, age-related macular degeneration, and atopic keratoconjunctivitis.

In particular, uveitis (Horai and Caspi, *J Interferon Cytokine Res*, 2011, 31, 733-744), diabetic retinopathy (Abcouwer, *J Clin Cell Immunol*, 2013, Suppl I, 1-12), diabetic macular edema (Sohn et al., *American Journal of Opthalmology*, 2011, 152, 686-694), dry eye disease (Stevenson et al, *Arch Ophthalmol*, 2012, 130, 90-100), and age-related macular degeneration (Knickelbein et al, *Int Ophthalmol Clin*, 2015, 55(3), 63-78) are characterized by elevation of certain pro-inflammatory cytokines that signal via the JAK-STAT pathway. Accordingly, compounds of the invention may be able to alleviate the associated ocular inflammation and reverse disease progression or provide symptom relief.

Retinal vein occlusion (RVO) is a highly prevalent visually disabling disease. Obstruction of retinal blood flow can lead to damage of the retinal vasculature, hemorrhage, and tissue ischemia. Although the causes for RVO are multifactorial, both vascular as well as inflammatory mediators have been shown to be important (Deobhakta et al, *International Journal of Inflammation*, 2013, article ID 438412). Cytokines which signal through the JAK-STAT pathway, such as IL-6 and IL-13, as well as other cytokines, such as MCP-1, whose production is driven in part by JAK-STAT pathway signaling, have been detected at elevated levels in ocular tissues of patients with RVO (Shchuko et al, *Indian Journal of Ophthalmology*, 2015, 63(12), 905-911). Accordingly, compound 1 may be able to alleviate the associated ocular inflammation and reverse disease progression or provide symptom relief in this disease. While many patients with RVO are treated by photocoagulation, this is an inherently destructive therapy. Anti-VEGF agents are also used, but they are only effective in a fraction of patients. Steroid medications that reduce the level of inflammation in the eye (Triamcinolone acetonide and dexamethasone implants) have also been shown to provide beneficial results for patients with certain forms of RVO, but they have also been shown to cause cataracts and increased intraocular pressure/glaucoma.

In one aspect, therefore, the invention provides a method of treating an ocular disease in a mammal, the method comprising administering 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol or a pharmaceutically-acceptable salt thereof to the eye of the mammal. In one aspect, the ocular disease is uveitis, diabetic retinopathy, diabetic macular edema, dry eye disease, age-related macular degeneration, retinal vein occlusion, or atopic keratoconjunctivitis. In one aspect, the method comprises administering the present compound by intravitreal injection.

Respiratory Diseases

The present compound, 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol (1) has demonstrated inhibition of T cell activation, inhibition of cytokines associated with inflammation, and activity in rodent lung eosinophilia and neutrophilia assays. Therefore, the compound is believed to be useful for the treatment of certain specific respiratory diseases.

Eosinophilic airway inflammation is a characteristic feature of diseases collectively termed eosinophilic lung diseases (Cottin et al., *Clin. Chest. Med.,* 2016, 37(3), 535-56). Eosinophilic diseases have been associated with IL-4, IL-13 and IL-5 signaling. Eosinophilic lung diseases include infections (especially helminthic infections), drug-induced pneumonitis (induced for example by therapeutic drugs such as antibiotics, phenytoin, or 1-tryptophan), fungal-induced pneumonitis (e.g. allergic bronchopulmonary aspergillosis), hypersensitivity pneumonitis and eosinophilic granulomatosis with polyangiitis (formerly known as Churg-Strauss syndrome). Eosinophilic lung diseases of unknown etiology include idiopathic acute eosinophilic pneumonia, idiopathic chronic eosinophilic pneumonia, hypereosinophilic syndrome, and Löffler syndrome. Compound 1 has been shown to significantly reduce lung eosinophilia in the rodent airway model of Assay 13 and to potently inhibit IL-13, IL-4, and IL-2 signaling in cellular assays.

A polymorphism in the IL-6 gene has been associated with elevated IL-6 levels and an increased risk of developing pulmonary arterial hypertension (PAH) (Fang et al., *J Am Soc Hypertens.,* Interleukin-6-572C/G polymorphism is associated with serum interleukin-6 levels and risk of idiopathic pulmonary arterial hypertension, 2017, ahead of print). Corroborating the role of TL-6 in PAH, inhibition of the IL-6 receptor chain gp130 ameliorated the disease in a rat model of PAH (Huang et al., *Can. J Cardiol.,* 2016, 32(11), 1356.e1-1356.e10). The compound of the invention has been shown to inhibit IL-6 signaling.

Cytokines such as IFNγ, IL-12 and IL-6 have been implicated in a range of non-allergic lung diseases such as sarcoidosis, and lymphangioleiomyomatosis (El-Hashemite et al., *Am. J. Respir. Cell Mol. Biol.,* 2005, 33, 227-230, and El-Hashemite et al., *Cancer Res.,* 2004, 64, 3436-3443). The compound of the invention has also been shown to inhibit IL-6 and IFNγ signaling.

Bronchiectasis and infiltrative pulmonary diseases are diseases associated with chronic neutrophilic inflammation. The compound of the invention has been shown to inhibit airway neutrophilia in a rodent model.

Pathological T cell activation is critical in the etiology of multiple respiratory diseases. Autoreactive T cells play a role in bronchiolitis obliterans organizing pneumonia (also termed COP [cryptogenic organizing pneumonia]). More recently, immune-checkpoint inhibitor induced pneumonitis, another T cell mediated lung disease emerged with the increased use of immune-checkpoint inhibitors. In cancer patients treated with these T cell stimulating agents, fatal pneumonitis can develop. The compound of the invention has been shown to inhibit activation in T cells isolated from human peripheral blood mononuclear cells.

In one aspect, therefore, the invention provides a method of treating a respiratory disease in a mammal (e.g., a human), the method comprising administering to the mammal 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol or a pharmaceutically acceptable salt thereof, or a pharmaceutical composition comprising a pharmaceutically-acceptable carrier and the compound of the invention, or a pharmaceutically acceptable salt thereof, wherein the respiratory disease is a lung infection, a helminthic infection, pulmonary arterial hypertension, sarcoidosis, lymphangioleiomyomatosis, bronchiectasis, or an infiltrative pulmonary disease.

In another aspect, the invention provides a method of treating a respiratory disease in a mammal (e.g., a human), the method comprising administering to the mammal the compound of the invention, or a pharmaceutically acceptable salt thereof, or a pharmaceutical composition comprising a pharmaceutically-acceptable carrier and the compound of the invention, or a pharmaceutically acceptable salt thereof, wherein the respiratory disease is drug-induced pneumonitis, fungal induced pneumonitis, allergic bronchopulmonary aspergillosis, hypersensitivity pneumonitis, eosinophilic granulomatosis with polyangiitis, idiopathic acute eosinophilic pneumonia, idiopathic chronic eosinophilic pneumonia, hypereosinophilic syndrome, Löffler syndrome, bronchiolitis obliterans organizing pneumonia, or immune-checkpoint-inhibitor induced pneumonitis.

JAK-signaling cytokines also play a major role in the activation of T cells, a sub-type of immune cells that is central to many immune processes. Pathological T cell activation is critical in the etiology of multiple respiratory diseases. Autoreactive T cells play a role in bronchiolitis obliterans organizing pneumonia (also termed COS). Similar to COS the etiology of lung transplant rejections is linked to an aberrant T cell activation of the recipients T cells by the transplanted donor lung. Lung transplant rejections may occur early as Primary Graft Dysfunction (PGD), organizing pneumonia (OP), acute rejection (AR) or lymphocytic bronchiolitis (LB) or they may occur years after lung transplantation as Chronic Lung Allograft Dysfunction (CLAD). CLAD was previously known as bronchiolitis obliterans (BO) but now is considered a syndrome that can have different pathological manifestations including BO, restrictive CLAD (rCLAD or RAS) and neutrophilic allograft dysfunction. Chronic lung allograft dysfunction (CLAD) is a major challenge in long-term management of lung transplant recipients as it causes a transplanted lung to progressively lose functionality (Gauthier et al., Curr Transplant Rep., 2016, 3(3), 185-191). CLAD is poorly responsive to treatment and therefore, there remains a need for effective compounds capable of preventing or treating this condition. Several JAK-dependent cytokines such as IFNγ and IL-5 are up-regulated in CLAD and lung transplant rejection (Berastegui et al, *Clin Transplant.* 2017, 31, e12898). Moreover, high lung levels of CXCR3 chemokines such as CXCL9 and CXCL10 which are downstream of JAK-dependent IFN signaling, are linked to worse outcomes in lung transplant patients (Shino et al, *PLOS One,* 2017, 12 (7), e0180281). Systemic JAK inhibition has been shown to be effective in kidney transplant rejection (Vicenti et al., *American Journal of Transplantation,* 2012, 12, 2446-56). Therefore, JAK inhibitors have the potential to be effective in treating or preventing lung transplant rejection and CLAD. Similar T cell activation events as described as the basis for lung transplant rejection also are considered the main driver of lung graft-versus-host disease (GVHD) which can occur post hematopoietic stem cell transplants. Similar to CLAD, lung GVHD is a chronic progressive condition with extremely poor outcomes and no treatments are currently approved. A retrospective, multicenter survey study of 95 patients with steroid-refractory acute or chronic GVHD who received the systemic JAK inhibitor ruxolitinib as salvage therapy demonstrated complete or partial response to ruxolitinib in the majority of patients including those with lung GVHD (Zeiser et al, *Leukemia,* 2015, 29, 10, 2062-68). As systemic JAK inhibition is associated with serious adverse events and a small therapeutic index, the need remains for an inhaled lung-directed, non-systemic JAK inhibitor to prevent and/or treat lung transplant rejection or lung GVHD.

Accordingly, the disclosure further provides a method of treating the additional respiratory conditions described above in a mammal, the method comprising administering to the mammal compound 1, or a pharmaceutically acceptable salt thereof.

Gastrointestinal Inflammatory Disease

As a JAK inhibitor, compound 1, or a pharmaceutical salt thereof, may also be useful to treat gastrointestinal inflammatory diseases that include, but are not limited to, inflammatory bowel disease, ulcerative colitis (proctosigmoiditis, pancolitis, ulcerative proctitis and left-sided colitis), Crohn's disease, collagenous colitis, lymphocytic colitis, Behcet's disease, celiac disease, immune checkpoint inhibitor induced colitis, ileitis, eosinophilic esophagitis, graft versus host disease-related colitis, and infectious colitis. Ulcerative colitis (Reimund et al., *J Clin Immunology,* 1996, 16, 144-150), Crohn's disease (Woywodt et al., *Eur J Gastroenterology Hepatology,* 1999, 11, 267-276), collagenous colitis (Kumawat et al., *Mol Immunology,* 2013, 55, 355-364), lymphocytic colitis (Kumawat et al., 2013), eosinophilic esophagitis (Weinbrand-Goichberg et al., *Immunol Res,* 2013, 56, 249-260), graft versus host disease-related colitis (Coghill et al., *Blood,* 2001, 117, 3268-3276), infectious colitis (Stallmach et al., *Int J Colorectal Dis,* 2004, 19, 308-315), Behcet's disease (Zhou et al., *Autoimmun Rev,* 2012, 11, 699-704), celiac disease (de Nitto et al., *World J Gastroenterol,* 2009, 15, 4609-4614), immune checkpoint inhibitor induced colitis (e.g., CTLA-4 inhibitor-induced colitis; (Yano et al., *J Translation Med,* 2014, 12, 191), PD-1- or PD-L1-inhibitor-induced colitis), and ileitis (Yamamoto et al., *Dig Liver Dis,* 2008, 40, 253-259) are characterized by elevation of certain pro-inflammatory cytokine levels. As many pro-inflammatory cytokines signal via JAK activation, compounds described in this application may be able to alleviate the inflammation and provide symptom relief.

Inflammatory Skin Disease

Atopic dermatitis and other inflammatory skin diseases have been associated with elevation of proinflammatory cytokines that rely on the JAK-STAT pathway. Therefore compound 1, or a pharmaceutical salt thereof, may be beneficial in a number of dermal inflammatory or pruritic conditions that include, but are not limited to atopic dermatitis, alopecia areata, vitiligo, psoriasis, dermatomyositis, cutaneous T cell lymphoma (Netchiporouk et al., *Cell Cycle.* 2014; 13, 3331-3335) and subtypes (Sezary syndrome, mycosis fungoides, pagetoid reticulosis, granulomatous slack skin, lymphomatoid papulosis, pityriasis lichenoides chronica, pityriasis lichenoides et varioliformis acuta, CD30+ cutaneous T-cell lymphoma, secondary cutaneous CD30+ large cell lymphoma, non-mycosis fungoides CD30− cutaneous large T-cell lymphoma, pleomorphic T-cell lymphoma, Lennert lymphoma, subcutaneous T-cell lymphoma, angiocentric lymphoma, blastic NK-cell lymphoma), prurigo nodularis, lichen planus, primary localized cutaneous amyloidosis, bullous pemphigoid, skin manifestations of graft versus host disease, pemphigoid, discoid lupus, granuloma annulare, lichen simplex chronicus, vulvar/scrotal/perianal pruritus, lichen sclerosus, post herpetic neuralgia itch, lichen planopilaris, and foliculitis decalvans. In particular, atopic dermatitis (Bao et al., *JAK-STAT,* 2013, 2, e24137), alopecia areata (Xing et al., *Nat Med.* 2014, 20, 1043-1049), vitiligo (Craiglow et al, *JAMA Dermatol.* 2015, 151, 1110-1112), prurigo nodularis (Sonkoly et al., *J Allergy Clin Immunol.* 2006, 117, 411-417), lichen planus (Welz-Kubiak et al., *J Immunol Res.* 2015, ID:854747), primary localized cutaneous amyloidosis (Tanaka et al., *Br J Dermatol.* 2009, 161, 1217-1224), bullous pemphigoid (Feliciani et al., *Int J Immunopathol Pharmacol.* 1999, 12, 55-61), and dermal manifestations of graft versus host disease (Okiyama et al., *J Invest Dermatol.* 2014, 134, 992-1000) are characterized by elevation of certain cytokines that signal via JAK activation. Accordingly, compound 1, or a pharmaceutically acceptable salt thereof, may be able to alleviate associated dermal inflammation or pruritus driven by these cytokines.

Other Diseases

Compound 1, or a pharmaceutically acceptable salt thereof, may also be useful to treat other diseases such as other inflammatory diseases, autoimmune diseases or cancers. Compound 1, or a pharmaceutically acceptable salt thereof, may be useful to treat one or more of arthritis, rheumatoid arthritis, juvenile rheumatoid arthritis, transplant rejection, xerophthalmia, psoriatic arthritis, diabetes, insulin dependent diabetes, motor neurone disease, myelodysplastic syndrome, pain, sarcopenia, cachexia, septic shock, systemic lupus erythematosus, leukemia, chronic lymphocytic leukemia, chronic myelocytic leukemia, acute lymphoblastic leukemia, acute myelogenous leukemia, ankylosing spondylitis, myelofibrosis, B-cell lymphoma, hepatocellular carcinoma, Hodgkins disease, breast cancer, Multiple myeloma, melanoma, non-Hodgkin lymphoma, non-small-cell lung cancer, ovarian clear cell carcinoma, ovary tumor, pancreas tumor, polycythemia vera, Sjoegrens syndrome, soft tissue sarcoma, sarcoma, splenomegaly, T-cell lymphoma, and thalassemia major.

Combination Therapy

Compound 1 of the disclosure or a pharmaceutically acceptable salt thereof may be used in combination with one or more agents which act by the same mechanism or by different mechanisms to treat a disease. The different agents may be administered sequentially or simultaneously, in separate compositions or in the same composition. Useful classes of agents for combination therapy include, but are not limited to, a beta 2 adrenoceptor agonist, a muscarinic receptor antagonist, a glucocorticoid agonist, a G-protein coupled receptor-44 antagonist, a leukotriene D4 antagonist, a muscarinic M3 receptor antagonist, a histamine H1 receptor antagonist, an immunoglobulin E antagonist, a PDE 4 inhibitor, an IL-4 antagonist, a muscarinic M1 receptor antagonist, a histamine receptor antagonist, an IL-13 antagonist, an IL-5 antagonist, a 5-Lipoxygenase inhibitor, a beta adrenoceptor agonist, a CCR3 chemokine antagonist, a CFTR stimulator, an immunoglobulin modulator, an interleukin 33 ligand inhibitor, a PDE 3 inhibitor, a phosphoinositide-3 kinase delta inhibitor, a thromboxane A2 antagonist, an elastase inhibitor, a Kit tyrosine kinase inhibitor, a leukotriene E4 antagonist, a leukotriene antagonist, a PGD2 antagonist, a TNF alpha ligand inhibitor, a TNF binding agent, a complement cascade inhibitor, an eotaxin ligand inhibitor, a glutathione reductase inhibitor, an histamine H4 receptor antagonist, an IL-6 antagonist, an IL2 gene stimulator, an immunoglobulin gamma Fc receptor IIB modulator, an interferon gamma ligand, an interleukin 13 ligand inhibitor, an interleukin 17 ligand inhibitor, a L-Selectin antagonist, a leukocyte elastase inhibitor, a leukotriene C4 antagonist, a Leukotriene C4 synthase inhibitor, a membrane copper amine oxidase inhibitor, a metalloprotease-12 inhibitor, a metalloprotease-9 inhibitor, a mite allergen modulator, a muscarinic receptor modulator, a nicotinic acetylcholine receptor agonist, a nuclear factor kappa B inhibitor, a p-Selectin antagonist, a PDE 5 inhibitor, a PDGF receptor antagonist, a phosphoinositide-3 kinase gamma inhibitor, a TLR-7 agonist, a TNF antagonist, an Abl tyrosine kinase inhibitor, an acetylcholine receptor antagonist, an acidic mammalian chitinase inhibitor, an ACTH receptor agonist, an actin polymerization modulator, an adenosine A1 receptor antagonist, an adenylate cyclase stimulator, an adrenoceptor antagonist, an adrenocorticotrophic hormone ligand, an alcohol dehydrogenase 5 inhibitor, an alpha 1 antitrypsin stimulator, an alpha 1 proteinase inhibitor, an androgen receptor modulator, an angiotensin converting enzyme 2 stimulator, an ANP agonist, a Bcr protein inhibitor, a beta 1 adrenoceptor antagonist, a beta 2 adrenoceptor antagonist, a beta 2 adrenoceptor modulator, a beta amyloid modulator, a BMP10 gene inhibitor, a BMP15 gene inhibitor, a calcium channel inhibitor, a cathepsin G inhibitor, a CCL26 gene inhibitor, a CCR3 chemokine modulator, a CCR4 chemokine antagonist, a cell adhesion molecule inhibitor, a chaperonin stimulator, a chitinase inhibitor, a collagen 1 antagonist, a complement C3 inhibitor, a CSF-1 antagonist, a CXCR2 chemokine antagonist, a cytokine receptor common beta chain modulator, a cytotoxic T-lymphocyte protein-4 stimulator, a deoxyribonuclease I stimulator, a deoxyribonuclease stimulator, a dipeptidyl peptidase 1 inhibitor, a DNA gyrase inhibitor, a DP prostanoid receptor modulator, an E-Selectin antagonist, an EGFR family tyrosine kinase receptor inhibitor, an elastin modulator, an Endothelin ET-A antagonist, an Endothelin ET-B antagonist, an epoxide hydrolase inhibitor, a FGF3 receptor antagonist, a Fyn tyrosine kinase inhibitor, a GATA 3 transcription factor inhibitor, a Glucosylceramidase modulator, a Glutamate receptor modulator, a GM-CSF ligand inhibitor, a Guanylate cyclase stimulator, a H+K+ ATPase inhibitor, an hemoglobin modulator, an Heparin agonist, an Histone deacetylase inhibitor, an Histone deacetylase-2 stimulator, an HMG CoA reductase inhibitor, an I-kappa B kinase beta inhibitor, an ICAM1 gene inhibitor, an IL-17 antagonist, an IL-17 receptor modulator, an IL-23 antagonist, an IL-4 receptor modulator, an Immunoglobulin G modulator, an Immunoglobulin GI agonist, an Immunoglobulin GI modulator, an Immunoglobulin epsilon Fc receptor IA antagonist, an Immunoglobulin gamma Fc receptor IIB antagonist, an Immunoglobulin kappa modulator, an Insulin sensitizer, an Interferon beta ligand, an Interleukin 1 like receptor antagonist, an Interleukin 18 ligand inhibitor, an Interleukin receptor 17A antagonist, an Interleukin-1 beta ligand inhibitor, an Interleukin-5 ligand inhibitor, an Interleukin-6 ligand inhibitor, a KCNA voltage-gated potassium channel-3 inhibitor, a Kit ligand inhibitor, a Laminin-5 agonist, a Leukotriene CysLT1 receptor antagonist, a Leukotriene CysLT2 receptor antagonist, a LOXL2 gene inhibitor, a Lyn tyrosine kinase inhibitor, a MARCKS protein inhibitor, a MDR associated protein 4 inhibitor, a Metalloprotease-2 modulator, a Metalloprotease-9 modulator, a Mineralocorticoid receptor antagonist, a Muscarinic M2 receptor antagonist, a Muscarinic M4 receptor antagonist, a Muscarinic M5 receptor antagonist, a Natriuretic peptide receptor A agonist, a Natural killer cell receptor modulator, a Nicotinic ACh receptor alpha 7 subunit stimulator, a NK cell receptor modulator, a Nuclear factor kappa B modulator, an opioid growth factor receptor agonist, a P-Glycoprotein inhibitor, a P2X3 purinoceptor antagonist, a p38 MAP kinase inhibitor, a Peptidase 1 modulator, a phospholipase A2 inhibitor, a phospholipase C inhibitor, a plasminogen activator inhibitor 1 inhibitor, a platelet activating factor receptor antagonist, a PPAR gamma agonist, a prostacyclin agonist, a protein tyrosine kinase inhibitor, a SH2 domain inositol phosphatase 1 stimulator, a signal transduction inhibitor, a sodium channel inhibitor, a STAT-3 modulator, a Stem cell antigen-1 inhibitor, a superoxide dismutase modulator, a T cell surface glycoprotein CD28 inhibitor, a T-cell surface glycoprotein CD8 inhibitor, a TGF beta agonist, a TGF beta antagonist, a thromboxane synthetase inhibitor, a thymic stromal lymphoprotein ligand inhibitor, a thymosin agonist, a thymosin beta 4 ligand, a TLR-8 agonist, a TLR-9 agonist, a TLR9 gene stimulator, a Topoisomerase IV inhibitor, a Troponin I fast skeletal muscle stimulator, a Troponin T fast skeletal muscle stimulator, a Type I IL-1 receptor antagonist, a Type II TNF receptor modulator, an ion channel modulator, a uteroglobin stimulator, and a VIP agonist.

Specific agents that may be used in combination with the present JAK inhibitor compound 1 include, but are not limited to rositor acetate, umeclidinium bromide, secukinumab, metenkefalin acetate, tridecactide acetate, fluticasone propionate, alpha-cyclodextrin-stabilized sulforaphane, tezepelumab, mometasone furoate, BI-1467335, dupilumab, aclidinium, formoterol, AZD-1419, HI-1640V, rivipansel, CMP-001, mannitol, ANB-020, omalizumab, tregalizumab, Mitizax, benralizumab, golimumab, roflumilast, imatinib, REGN-3500, masitinib, apremilast, RPL-554, Actimmune, adalimumab, rupatadine, parogrelil, MK-1029, beclometasone dipropionate, formoterol fumarate, mogamulizumab, seratrodast, UCB-4144, nemiralisib, CK-2127107, fevipiprant, danirixin, bosentan, abatacept, EC-18, duvelisib, dociparstat, ciprofloxacin, salbutamol HFA, erdosteine, PrEP-001, nedocromil, CDX-0158, salbutamol, enobosarm, R-TPR-022, lenzilumab, fluticasone furoate, vilanterol trifenatate, fluticasone propionate, salmeterol, PT-007, PRS-060, remestemcel-L, citrulline, RPC-4046, nitric oxide, DS-102, gerilimzumab, Actair, fluticasone furoate, umeclidinium, vilanterol, AG-NPP709, Gamunex, infliximab, Ampion, acumapimod, canakinumab, INS-1007, CYP-001, sirukumab, fluticasone propionate, mepolizumab, pitavastatin, solithromycin, etanercept, ivacaftor, anakinra, MPC-300-IV, glycopyrronium bromide, aclidinium bromide, FP-025, risankizumab, glycopyrronium, formoterol fumarate, Adipocell, YPL-001, tiotropium bromide, glycopyrronium bromide, indacaterol maleate, andecaliximab, olodaterol, esomeprazole, dust mite vaccine, mugwort pollen allergen vaccine, vamorolone, gefapixant, revefenacin, gefitinib, ReJoin, tipelukast, bedoradrine, SCM-CGH, SHP-652, RNS-60, brodalumab, BIO-11006, umeclidinium bromide, vilanterol trifenatate, ipratropium bromide, tralokinumab, PUR-1800, VX-561, VX-371, olopatadine, tulobuterol, formoterol fumarate, triamcinolone acetonide, reslizumab, salmeterol xinafoate, fluticasone propionate, beclometasone dipropionate, formoterol fumarate, tiotropium bromide, ligelizumab, RUTI, bertilimumab, omalizumab, glycopyrronium bromide, SENS-111, beclomethasone dipropionate, CHF-5992, LT-4001, indacaterol, glycopyrronium bromide, mometasone furoate, fexofenadine, glycopyrronium bromide, azithromycin, AZD-7594, formoterol, CHF-6001, batefenterol, OATD-01, olodaterol, CJM-112, rosiglitazone, salmeterol, setipiprant, inhaled interferon beta, AZD-8871, plecanatide, fluticasone, salmeterol, eicosapentaenoic acid monoglycerides, lebrikizumab, RG-6149, QBKPN, Mometasone, indacaterol, AZD-9898, sodium pyruvate, zileuton, CG-201, imidafenacin, CNTO-6785, CLBS-03, mometasone, RGN-137, procaterol, formoterol, CCI-15106, POL-6014, indacaterol, beclomethasone, MV-130, GC-1112, Allergovac depot, MEDI-3506, QBW-251, ZPL-389, udenafil, GSK-3772847, levocetirizine, AXP-1275, ADC-3680, timapiprant, abediterol, AZD-7594, ipratropium bromide, salbutamol sulfate, tadekinig alfa, ACT-774312, dornase alfa, iloprost, batefenterol, fluticasone furoate, alicaforsen, ciclesonide, emeramide, arformoterol, SB-010, Ozagrel, BTT-1023, Dectrekumab, levalbuterol, pranlukast, hyaluronic acid, GSK-2292767, Formoterol, NOV-14, Lucinactant, salbutamol, prednisolone, ebastine, dexamethasone cipecilate, GSK-2586881, BI-443651, GSK-2256294, VR-179, VR-096, hdm-ASIT+, budesonide, GSK-2245035, VTX-1463, Emedastine, dexpramipexole, levalbuterol, N-6022, dexamethasone sodium phosphate, PIN-201104, OPK-0018, TEV-48107, suplatast, BI-1060469, Gemilukast, interferon gamma, dalazatide, bilastine, fluticasone propionate, salmeterol xinafoate, RP-3128, bencycloquidium bromide, reslizumab, PBF-680, CRTH2 antagonist, Pranlukast, salmeterol xinafoate, fluticasone propionate, tiotropium bromide monohydrate, masilukast, RG-7990, Doxofylline, abediterol, glycopyrronium bromide, TEV-46017, ASM-024, fluticasone propionate, glycopyrronium bromide, salmeterol xinafoate, salbutamol, TA-270, Flunisolide, sodium chromoglycate, Epsi-gam, ZPL-521, salbutamol, aviptadil, TRN-157, Zafirlukast, Stempeucel, pemirolast sodium, nadolol, fluticasone propionate+salmeterol xinafoate, RV-1729, salbutamol sulfate, carbon dioxide+perfluorooctyl bromide, APL-1, dectrekumab+VAK-694, lysine acetylsalicylate, zileuton, TR-4, human allogenic adipose-derived mesenchymal progenitor cell therapy, MEDI-9314, PL-3994, HMP-301, TD-5471, NKTT-120, pemirolast, beclomethasone dipropionate, trantinterol, monosodium alpha luminol, IMD-1041, AM-211, TBS-5, ARRY-502, seratrodast, recombinant midismase, ASM-8, deflazacort, bambuterol, RBx-10017609, ipratropium+fenoterol, fluticasone+formoterol, epinastine, WIN-901X, VALERGEN-DS, OligoG-COPD-5/20, tulobuterol, oxis Turbuhaler, DSP-3025, ASM-024, mizolastine, budesonide+salmeterol, LH-011, AXP-E, histamine human immunoglobulin, YHD-001, theophylline, ambroxol+erdosteine, ramatroban, montelukast, pranlukast, AG-1321001, tulobuterol, ipratropium+salbutamol, tranilast, methylprednisolone suleptanate, colforsin daropate, repirinast, and doxofylline.

Also provided, herein, is a pharmaceutical composition comprising compound 1, or a pharmaceutically acceptable salt thereof and one or more other therapeutic agents. The therapeutic agent may be selected from the class of agents specified above and from the list of specific agent described above. In some embodiments, the pharmaceutical composition is suitable for delivery to the lungs. In some embodiments, the pharmaceutical composition is suitable for inhaled or nebulized administration. In some embodiments, the pharmaceutical composition is a dry powder or a liquid composition.

Further, in a method aspect, the invention provides a method of treating a disease or disorder in a mammal comprising administering to the mammal compound 1 or a pharmaceutically acceptable salt thereof and one or more other therapeutic agents.

When used in combination therapy, the agents may be formulated in a single pharmaceutical composition, or the agents may be provided in separate compositions that are administered simultaneously or at separate times, by the same or by different routes of administration. Such compositions can be packaged separately or may be packaged together as a kit. The two or more therapeutic agents in the kit may be administered by the same route of administration or by different routes of administration.

The compound of the invention has been demonstrated to be a potent inhibitor of the JAK1, JAK2, JAK3, and TYK2 enzymes in enzyme binding assays, to have potent functional activity without cytotoxicity in cellular assays, and to exert the pharmacodynamic effects of JAK inhibition in preclinical models, as described in the following examples.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

ACN=acetonitrile
DCC=dicyclohexylcarbodiimide
DIPEA=N,N-diisopropylethylamine
DMF=N,N-dimethylformamide
EtOAc=ethyl acetate
HATU=N,N,N',N'-tetramethyl-O-(7-azabenzotriazol-1-yl)uronium hexafluorophosphate
LDA=lithium diisopropylamide
min=minute(s)
MTBE=methyl tert-butyl ether
NBS=N-bromosuccinimide
RT=room temperature
THF=tetrahydrofuran
bis(pinacolato)diboron=4,4,5,5,4',4',5',5'-octamethyl-[2,2']bi[[1,3,2]dioxaborolanyl]
Pd(dppf)Cl$_2$—CH$_2$Cl$_2$=dichloro(1,1'-bis(diphenylphosphino)-ferrocene)-dipalladium(II) complex with dichloromethane Reagents and solvents were purchased from commercial suppliers (Aldrich, Fluka, Sigma, etc.), and used without further purification. Progress of reaction mixtures was monitored by thin layer chromatography (TLC), analytical high performance liquid chromatography (anal. HPLC), and mass spectrometry. Reaction mixtures were worked up as described specifically in each reaction; commonly they were purified by extraction and other purification methods such as temperature-, and solvent-dependent crystallization, and precipitation. In addition, reaction mixtures were routinely purified by column chromatography or by preparative HPLC, typically using C18 or BDS column packings and conventional eluents. Typical preparative HPLC conditions are described below.

Characterization of reaction products was routinely carried out by mass and ¹H-NMR spectrometry. For NMR analysis, samples were dissolved in deuterated solvent (such as CD₃OD, CDCl₃, or d₆-DMSO), and ¹H-NMR spectra were acquired with a Varian Gemini 2000 instrument (400 MHz) under standard observation conditions. Mass spectrometric identification of compounds was performed by an electrospray ionization method (ESMS) with an Applied Biosystems (Foster City, Calif.) model API 150 EX instrument or a Waters (Milford, Mass.) 3100 instrument, coupled to autopurification systems.

Preparative HPLC Conditions

Column: C18, 5 µm. 21.2×150 mm or C18, 5 µm 21×250 or C14, 5 µm 21×150 mm

Column temperature: Room Temperature

Flow rate: 20.0 mL/min

Mobile Phases: A=Water+0.05% TFA
B=ACN+0.05% TFA,

Injection volume: (100-1500 µL)

Detector wavelength: 214 nm

Crude compounds were dissolved in 1:1 water:acetic acid at about 50 mg/mL. A 4 minute analytical scale test run was carried out using a 2.1×50 mm C18 column followed by a 15 or 20 minute preparative scale run using 100 µL injection with the gradient based on the % B retention of the analytical scale test run. Exact gradients were sample dependent. Samples with close running impurities were checked with a 21×250 mm C18 column and/or a 21×150 mm C14 column for best separation. Fractions containing desired product were identified by mass spectrometric analysis.

Analytic HPLC Conditions

Method A

Column: Agilent Zorbax Bonus-RP C18, 150×4.60 nm, 3.5 micron

Column temperature; 40° C.

Flow rate: 1.5 mL/min

Injection volume: 5 µL

Sample preparation: Dissolve in 1:1 ACN:1 M HCl

Mobile Phases; A=Water:TFA (99.95:0.05)
B=ACN:TFA (99.95:0.05)

Detector wavelength: 254 nm and 214 nm

Gradient: 26 min total (time (min)/% B): 0/5, 18/90, 22/90, 22.5/90, 26/5

Method B

Column: Agilent Poroshell 120 Bonus-RP, 4.6×150 mm, 2.7 µm

Column temperature: 30° C.

Flow rate; 1.5 mL/min

Injection volume: 10 µL

Mobile Phases: A=ACN:Water:TFA (2:98:0.1)
B=ACN:Water:TFA (90:10:0.1)

Sample preparation: Dissolve in Mobile phase B

Detector wavelength: 254 nm and 214 nm

Gradient: 60 min total (time (min)/% B): 0/0, 50/100, 55/100, 55.1/0, 60/0

Preparation 1:
1-benzyl-4-imino-1,4-dihydropyridin-3-amine

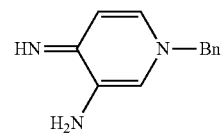 [SMILES: N=c1ccn(Cc2ccccc2)cc1N]

A mixture of pyridine-3,4-diamine (445 g, 4.078 mol) and ACN (11.0 L) was stirred for 80 min from 25° C. to 15° C. Benzyl bromide (485 mL, 4.078 mol) was added over 20 min and the reaction mixture was stirred at 20° C. overnight. The reaction mixture was cooled to 10° C. and filtered. To the reactor was added ACN (3 L), which was cooled to 10° C. The cake was washed with the reactor rinse and washed again with ACN (3 L) warmed to 25° C. The solid was dried on the filter for 24 h under nitrogen, at 55° C. under vacuum for 2 h and then at RT overnight and for 4 d to provide the HBr salt of the title compound (1102.2 g, 3.934 mol, 96% yield). HPLC Method A Retention time 4.12 min.

Preparation 2: 5-Benzyl-2-(6-bromo-1H-indazol-3-yl)-5H-imidazo[4,5-c]pyridine

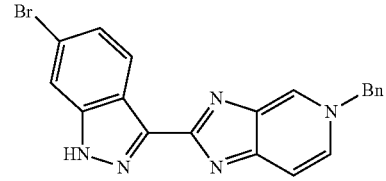 [SMILES: Brc1ccc2c(-c3nc4ccn(Cc5ccccc5)cc-4n3)n[nH]c2c1]

(a) 5-Benzyl-2-(6-bromo-1H-indazol-3-yl)-5H-imidazo[4,5-c]pyridine

A solution of 6-bromo-1H-indazole-3-carbaldehyde (550 g, 2.444 mol), 1-benzyl-4-imino-1,4-dihydropyridin-3-amine HBr (721 g, 2.333 mol) and DMAc (2.65 L) was stirred for 60 min and sodium bisulfite (257 g, 2.468 mol) was added. The reaction mixture was heated to 135° C. and held for 3 h, and allowed to cool to 20° C. and held at 20° C. overnight. Acetonitrile (8 L) was added and the reaction mixture was stirred for 4 h at 15° C. The slurry was filtered on a pressure filter at medium filtration rate. To the reactor was added ACN (1 L) The cake was washed with the ACN reactor wash and dried under nitrogen overnight and then under vacuum at 50° C. for 24 h to provide the HBr salt of the title compound (1264 g, 2.444 mol, 100% yield, 94% purity) as a dense wet beige/brown solid. HPLC Method A Retention time 8.77 min.

A mixture of the product of the previous step (1264 g, 2.444 mol), MeTHF (6 L) and water (2.75 L) was heated to 65° C. and sodium hydroxide 50 wt % (254 g, 3.177 mol) was added over 5 min and the reaction mixture was stirred at 65° C. for 1 h, cooled to RT, then to 5° C. and held for 2 h. The slurry was filtered and the reactor and cake were washed with MeTHF (1 L). The resulting beige to yellow solid was dried on the filter under nitrogen for 3 d to provide the title compound (475 g, 1.175 mmol, 48% yield) as a beige/yellow solid. The mother liquor (about 8 L) was concentrated to about 2 L, whereupon solids began to crash out. The slurry was heated to 50° C., held for 2 h, cooled to 5° C. over 2 h, stirred overnight, and filtered. The cake was washed with MeTHF (100 mL) and dried overnight under vacuum at 40° C. to provide additional title compound (140 g, 0.346 mol, 14% yield).

A mixture of the total product of the previous step, combined with the product of a second batch at the same scale (1500 g, 3.710 mol) and MeTHF (4 L) was stirred at 20° C. for 2 h and filtered. The reactor and cake were washed with MeTHF (1.5 L). The resulting beige to yellow solid was dried under nitrogen for 3 d to provide the title compound as a beige yellow solid (1325 g, 3.184 mol, 86% yield (overall 68% yield), 97% purity). HPLC Method A Retention time 8.77 min Preparation 3: 5-benzyl-2-(6-bromo-1H-indazol-3-yl)-4,5,6,7-tetrahydro-1H-imidazo[4,5-c]pyridine

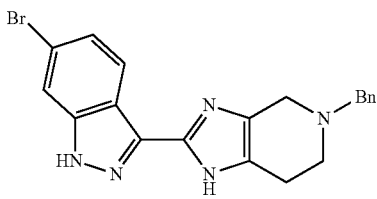 [SMILES: Brc1ccc2c(-c3nc4c([nH]3)CCN(Cc3ccccc3)C4)n[nH]c2c1]

To a 15 L flask was added 5-benzyl-2-(6-bromo-1H-indazol-3-yl)-5H-imidazo[4,5-c]pyridine (440 g, 1.088 mol) followed by MeTHF (4.5 L), methanol (2.25 L) and water (1.125 L). The slurry was cooled to 20° C., stirred for 1 h, and NaBH$_4$ (247 g, 6.530 mol) was added. The reaction mixture was stirred at 25° C. for 18 h. Water (1.125 L) was added followed by 20 wt %. sodium chloride solution (1.125 L) and the mixture was stirred for 30 min and the layers allowed to separate. The aqueous layer was drained. A premixed solution of NaOH (522 g) and water (5 L) was added and the reaction mixture was stirred for 60 min; the layers were allowed to separate and the aqueous layer was drained. Two additional batches at the same scale were prepared.

The organic layer from one batch was concentrated under reduced pressure in a 15 L jacketed reactor with the jacket set at 50° C., internal temperature 20° C. The additional batches were added to the reactor and concentrated one at a time resulting in a slurry about 6 L in volume. The slurry was heated to 50° C., IPAc (6 L) was added and the mixture was held at 60° C. for 1.5 h, cooled to 20° C. for 10 h, heated to 60° C. for 50 h, cooled to 20° C. in 5 h, then cooled to 5° C. and held for 3 h. The mixture was filtered and the reactor and cake was washed with a premixed solution of IPAc (1 L) and MeTHF (1 L), precooled to 5° C. The solids were dried under nitrogen on the filter at 40° C. for 3 d to provide the title compound (1059 g, 2.589 mol, 79% yield) as an off-white solid. The material was further dried in a vacuum oven at 50-60° C. for 8 h and at 27° C. for 2 d to provide the title compound (1043 g, 2.526 mol, 77% yield, 99% purity). HPLC Method A Retention time 6.73 min.

Preparation 4: (4-(Benzyloxy)-2-ethyl-5-fluorophenyl)trifluoroborate, Potassium

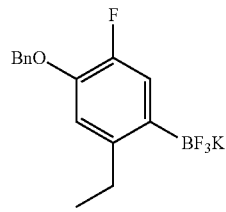

(a) 2-(4-(Benzyloxy)-2-ethyl-5-fluorophenyl)-4,4,5,5-tetramethyl-1,3,2-dioxaborolane A mixture of 1-(benzyloxy)-4-bromo-5-ethyl-2-fluorobenzene (520 g, 1682 mmol) and dioxane (5193 mL) was purged with nitrogen and then bis(pinacolato)diboron (641 g, 2523 mmol) was added followed by potassium acetate (495 g, 5046 mmol). The reaction mixture was purged with nitrogen; Pd(dppf)Cl$_2$ (41.2 g, 50.5 mmol) was added; the reaction mixture was purged with nitrogen, heated at 103° C. under nitrogen for 5 h; and cooled to RT. The reaction mixture was concentrated by vacuum distillation and partitioned between ethyl acetate (5204 mL) and water (5212 mL). The reaction mixture was filtered through Celite; the organic layer was washed with brine (2606 mL) followed by solvent removal by vacuum distillation to provide crude product as a thick black oil (~800 g).

The crude product was dissolved in DCM (1289 mL) and purified by silica gel chromatography (2627 g silica preslurried in hexane, eluted with 20% ethyl acetate in hexanes (10.35 L)). Solvent was removed by vacuum distillation to yield a light yellow oil (600 g). HPLC Method B Retention time 33.74 min.

(b) (4-(benzyloxy)-2-ethyl-5-fluorophenyl)trifluoroborate, Potassium

The product of the previous step (200 g, 561 mmol) was mixed with acetone (1011 mL) until complete dissolution and methanol (999 mL) was added followed by 3 M potassium hydrogen difluoride (307 g, 3930 mmol) dissolved in water (1310 mL). The reaction mixture was stirred for 3.5 h. Most of the organic solvent was removed by vacuum distillation. Water (759 mL) was added and the resulting thick slurry was stirred for 30 min and filtered. The cake was washed with water (506 mL) and the solids were dried on the filter for 30 min. The solids were slurried in acetone (1237 mL) and stirred for 1 h. The resulting slurry was filtered and the solids washed with acetone (247 mL). The acetone solution was concentrated by vacuum distillation, and a constant volume (2 L) was maintained by slow addition of toluene (2983 mL) until all acetone and water had been distilled. The toluene solution was distilled to a thick yellow slurry by rotary evaporation, during which time the products precipitated as white solids. An additional portion of toluene (477 mL) was added to the mixture and stirred for 1 h. The mixture was then filtered and rinsed with toluene (179 mL) and dried under vacuum at 50° C. for 24 h to provide the title compound (104 g, 310 mmol, 55% yield) as a free-flowing, fluffy, slightly off-white solid. HPLC Method B Retention time 27.71 min.

Preparation 5: 5-Benzyl-2-(6-(4-(benzyloxy)-2-ethyl-5-fluorophenyl)-1H-indazol-3-yl)-4,5,6,7-tetrahydro-1H-imidazo[4,5-c]pyridine

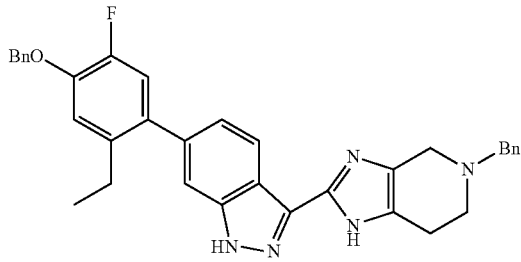 [SMILES: CCc1cc(OCc2ccccc2)c(F)cc1-c1ccc2c(-c3nc4c([nH]3)CCN(Cc3ccccc3)C4)n[nH]c2c1]

(a) 5-Benzyl-2-(6-(4-(benzyloxy)-2-ethyl-5-fluorophenyl)-1H-indazol-3-yl)-4,5,6,7-tetrahydro-1H-imidazo[4,5-c]pyridine A mixture of bis(pinacolato)diboron (250 g, 984 mmol) and IPA (1.88 L) was stirred to dissolution and then a solution of potassium hydrogen difluoride (538 g, 6.891 mol) in water (2.31 L) was added portion-wise over 10 min. The reaction mixture was stirred for 1 h and filtered. The gel-like solids were slurried with water (1.33 L) until the mixture formed a clear hydrogel and then for another 45 min. The resulting solids/gel were filtered, then reslurried in acetone (1.08 L), filtered, air dried on the filter for 30 min and dried overnight to provide a fluffy white solid (196.7 g).

To a 5 L flask was added 5-benzyl-2-(6-bromo-1H-indazol-3-yl)-4,5,6,7-tetrahydro-1H-imidazo[4,5-c]pyridine (135 g, 331 mmol), (4-(benzyloxy)-2-ethyl-5-fluorophenyl)-trifluoroborate, potassium (133 g, 397 mmol), and the white solid product of the previous step (40.5 g) followed by MeTHF (1.23 L) and MeOH (1.75 L). The resulting slurry was degassed three times with nitrogen. To the slurry was added a degassed solution of cesium carbonate (431 g, 1.323 mol) in water (1.35 L). The slurry was degassed twice, Pd (amphos)$_2$Cl$_2$ (11.71 g, 16.53 mmol) was added, the slurry was again degassed twice and the reaction mixture was stirred at 67° C. overnight and cooled to 20° C. The layers were separated and back extracted with MeTHF (550 mL). The organic layers were combined and concentrated by rotary evaporation until solids precipitated. MeTHF (700 mL) was added and the reaction mixture was stirred at 65° C. The layers were separated and the aqueous phase back extracted with MeTHF (135 mL). The organic phases were combined and concentrated to about 300 mL resulting in a thick orange slurry. To the slurry was added MeOH (270 mL) followed by 1M HCl (1.325 L) at 20° C. with rapid stirring. The reaction mixture was stirred for 5 min and water (1 L) was added and the resulting slurry was stirred for 1 h. The solids were filtered, washed with water (150 mL), dried on the filter for 10 min and at 45° C. under nitrogen for 16 h to provide the 2 HCl salt of the title compound (221.1 g, 351 mmol, 92.2% purity) as a light yellow solid. HPLC Method B retention time 23.41 min.

Preparation 6: 5-ethyl-2-fluoro-4-(3-(4,5,6,7-tetrahydro-1H-imidazo[4,5-c]pyridin-2-yl)-1H-indazol-6-yl)phenol

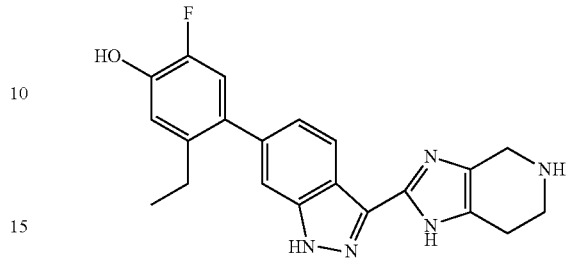

To a 1 L flask was added 5-benzyl-2-(6-(4-(benzyloxy)-2-ethyl-5-fluorophenyl)-1H-indazol-3-yl)-4,5,6,7-tetrahydro-1H-imidazo[4,5-c]pyridine, 2 HCl (40 g, 63.4 mmol) as a slurry in ethanol (348 mL) and 1.25 M HCl in MeOH (101 mL) and water (17.14 mL). The reaction mixture was degassed with nitrogen for 5 min and 10 wt % Pd/C, 50 wt % H$_2$O (4.05 g, 1.903 mmol) was added. The reactor was sealed, purged with H$_2$ pressurized to 1-2 psi. warmed to 50° C., and the reaction mixture was stirred overnight and filtered through Celite. The reactor and filter were washed with methanol (100 mL).

The filtered solution was combined with the product of a second batch at the 98 mmol scale and concentrated to 390 g. EtOAc (2.04 L) was added slowly with stirring and then the solution was cooled to 5° C. with stirring. Solids were filtered, washed with EtOAc (510 mL), and dried overnight at 45° C. under nitrogen to provide the 2 HCl salt of the title compound (58 g, 80% yield) as an off-white solid. HPLC Method B retention time 12.83 min.

Example 1: Crystalline hydrate of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol

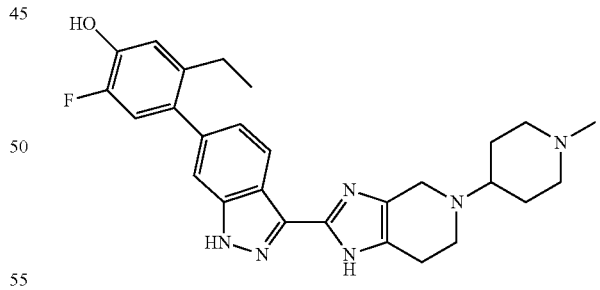

To a 3 L flask was added NMP (239 mL) and 5-ethyl-2-fluoro-4-(3-(4,5,6,7-tetrahydro-1H-imidazo[4,5-c]pyridin-2-yl)-1H-indazol-6-yl)phenol, 2 HCl (74.5 g, 165 mmol) with stirring followed by NMP (74 mL). Acetic acid (31.3 mL) was added and the reaction mixture was warmed to 55° C. for 10 min and then cooled to 25° C. 1-methylpiperidin-4-one (61.0 mL, 496 mmol) was added in a single portion and the reaction mixture was stirred at 25° C. for 30 min and cooled to 15° C. Sodium triacetoxyborohydride (98 g, 463 mmol) was added and the external jacket was set to 20° C. after 5 min. After 3 h, ammonium hydroxide (365 mL, 5790 mmol) was added dropwise over 45 min maintaining the temperature below 25° C. The reaction mixture was stirred for 1.5 h at 20° C., forming an off-white slurry. Methanol (709 mL) was added and the reaction mixture was stirred slowly overnight at 55° C. Water (1.19 L) was added over 30 min at 55° C. and the mixture was cooled to 10° C., stirred for 2 h, and filtered. The cake was washed with 1:1 MeOH:water (334 mL), dried on the filter for 20 min and at 45° C. under vacuum with nitrogen bleed to provide yellow solids (87 g).

To the solids was added 5% water/acetone (1.5 L) at 55° C. with slow stirring and the reaction mixture was heated at 55° C. for 6 h, cooled to 10° C., filtered, and washed with 5% water/acetone (450 mL). The solids were dried overnight at 50° C. under vacuum with nitrogen bleed, equilibrated in air for 20 h, dried in the vacuum oven for 48 h and equilibrated with air to provide the title compound (71.3 g, 91% yield) as a free flowing pale yellow solid. HPLC Method B Retention time 12.29 min.

Example 2: Powder X-Ray Diffraction

The powder X-ray diffraction (PXRD) pattern of the product of Example 1 was obtained with a Bruker D8-Advance X-ray diffractometer using Cu-Kα radiation ($\lambda$=1.54051 Å) with output voltage of 45 kV and current of 40 mA. The instrument was operated in Bragg-Brentano geometry with incident, divergence, and scattering slits set to maximize the intensity at the sample. For measurement, a small amount of powder (5-25 mg) was gently pressed onto a sample holder to form a smooth surface and subjected to X-ray exposure. The samples were scanned in 20-20 mode from 2° to 400 in 20 with a step size of 0.02° and a scan speed of 0.30° seconds per step. The data acquisition was controlled by Bruker DiffracSuite measurement software and analyzed by Jade software (version 7.5.1). The instrument was calibrated with a corundum standard, within ±0.02° two-theta angle. Observed PXRD two-theta peak positions and d-spacings are shown in Table1.

TABLE 1

PXRD Data for the Crystalline Hydrate

| 2-Theta | d(Å) | Area | A % |
|---|---|---|---|
| 6.20 | 14.24 | 81639 | 45.70 |
| 9.58 | 9.22 | 178629 | 100.00 |
| 10.34 | 8.55 | 30022 | 16.80 |
| 10.65 | 8.30 | 12801 | 7.20 |
| 11.54 | 7.66 | 27220 | 15.20 |
| 12.77 | 6.93 | 27705 | 15.50 |
| 13.01 | 6.80 | 48785 | 27.30 |
| 13.39 | 6.61 | 9261 | 5.20 |
| 16.94 | 5.23 | 40031 | 22.40 |
| 17.53 | 5.05 | 83718 | 46.90 |
| 18.67 | 4.75 | 9542 | 5.30 |
| 19.28 | 4.60 | 152922 | 85.60 |
| 20.02 | 4.43 | 22391 | 12.50 |
| 20.61 | 4.31 | 30308 | 17.00 |
| 21.51 | 4.13 | 92875 | 52.00 |
| 22.10 | 4.02 | 37495 | 21.00 |
| 22.79 | 3.90 | 13802 | 7.70 |
| 23.22 | 3.83 | 12117 | 6.80 |
| 25.16 | 3.54 | 13792 | 7.70 |
| 28.80 | 3.10 | 14487 | 8.10 |
| 29.62 | 3.01 | 14810 | 8.30 |
| 30.20 | 2.96 | 9709 | 5.40 |

Biological Assays 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol (compound 1) has been characterized in the following biological assays.

Assay 1: Biochemical JAK Kinase Assays

A panel of four LanthaScreen JAK biochemical assays (JAK1, 2, 3 and Tyk2) were carried in a common kinase reaction buffer (50 mM HEPES, pH 7.5, 0.01% Brij-35, 10 mM $MgCl_2$, and 1 mM EGTA). Recombinant GST-tagged JAK enzymes and a GFP-tagged STAT1 peptide substrate were obtained from Life Technologies.

The serially diluted compound was pre-incubated with each of the four JAK enzymes and the substrate in white 384-well microplates (Corning) at ambient temperature for 1 h. ATP was subsequently added to initiate the kinase reactions in 10 μL total volume, with 1% DMSO. The final enzyme concentrations for JAK1, 2, 3 and Tyk2 are 4.2 nM, 0.1 nM, 1 nM, and 0.25 nM respectively; the corresponding Km ATP concentrations used are 25 μM, 3 μM, 1.6 μM, and 10 μM; while the substrate concentration is 200 nM for all four assays. Kinase reactions were allowed to proceed for 1 hour at ambient temperature before a 10 μL preparation of EDTA (10 mM final concentration) and Tb-anti-pSTAT1 (pTyr701) antibody (Life Technologies, 2 nM final concentration) in TR-FRET dilution buffer (Life Technologies) was added. The plates were allowed to incubate at ambient temperature for 1 h before being read on the EnVision reader (Perkin Elmer). Emission ratio signals (520 nm/495 nm) were recorded and utilized to calculate the percent inhibition values based on DMSO and background controls.

For dose-response analysis, percent inhibition data were plotted vs. compound concentrations, and $IC_{50}$ values were determined from a 4-parameter robust fit model with the Prism software (GraphPad Software). Results were expressed as $pIC_{50}$ (negative logarithm of $IC_{50}$) and subsequently converted to $pK_i$ (negative logarithm of dissociation constant, Ki) using the Cheng-Prusoff equation.

The compound of the invention exhibited the following enzyme potency.

TABLE 2

| JAK 1 $pK_i$ | JAK 2 $pK_i$ | JAK 3 $pK_i$ | Tyk2 $pK_i$ |
|---|---|---|---|
| 10.2 | 10.8 | 9.7 | 9.8 |

Assay 2: Cellular JAK Potency Assay: Inhibition of IL-13

The AlphaScreen JAKI cellular potency assay was carried out by measuring interleukin-13 (IL-13, R&D Systems) induced STAT6 phosphorylation in BEAS-2B human lung epithelial cells (ATCC). The anti-STAT6 antibody (Cell Signaling Technologies) was conjugated to AlphaScreen acceptor beads (Perkin Elmer), while the anti-pSTAT6 (pTyr641) antibody (Cell Signaling Technologies) was biotinylated using EZ-Link Sulfo-NHS-Biotin (Thermo Scientific).

BEAS-2B cells were grown at 37° C. in a 5% $CO_2$ humidified incubator in 50% DMEM/50% F-12 medium (Life Technologies) supplemented with 10% FBS (Hyclone), 100 U/mL penicillin, 100 μg/mL streptomycin (Life Technologies), and 2 mM GlutaMAX (Life Technologies). On day 1 of the assay, cells were seeded at a 7,500 cells/well density in white poly-D-lysine-coated 384-well plates (Corning) with 25 μL medium, and were allowed to adhere overnight in the incubator. On day 2 of the assay, the medium was removed and replaced with 12 μL of assay buffer (Hank's Balanced Salt Solution/HBSS, 25 mM HEPES, and 1 mg/ml bovine serum albumin/BSA) containing dose-responses of test compounds. The compound was serially diluted in DMSO and then diluted another 1000-fold in media to bring the final DMSO concentration to 0.1%. Cells were incubated with test compounds at 37° C. for 1 h, and followed by the addition of 12 µl of pre-warmed IL-13 (80 ng/mL in assay buffer) for stimulation. After incubating at 37° C. for 30 min, the assay buffer (containing compound and IL-13) was removed, and 10 µL of cell lysis buffer (25 mM HEPES, 0.1% SDS, 1% NP-40, 5 mM $MgCl_2$, 1.3 mM EDTA, 1 mM EGTA, and supplement with Complete Ultra mini protease inhibitors and PhosSTOP from Roche Diagnostics). The plates were shaken at ambient temperature for 30 min before the addition of detection reagents. A mixture of biotin-anti-pSTAT6 and anti-STAT6 conjugated acceptor beads was added first and incubated at ambient temperature for 2 h, followed by the addition of streptavidin conjugated donor beads (Perkin Elmer). After a minimum of 2 h incubation, the assay plates were read on the EnVision plate reader. AlphaScreen luminescence signals were recorded and utilized to calculate the percent inhibition values based on DMSO and background controls.

For dose-response analysis, percent inhibition data were plotted vs. compound concentrations, and $IC_{50}$ values were determined from a 4-parameter robust fit model with the Prism software. Results may also be expressed as the negative logarithm of the $IC_{50}$ value, $pIC_{50}$. The compound of the invention exhibited a $pIC_{50}$ value of 8.2 in this assay.

Assay 3: Cellular JAK Potency Assay: Inhibition of IL-2/Anti-CD3 Stimulated IFNγ in Human PBMCs The potency of the test compound for inhibition of interleukin-2 (IL-2)/anti-CD3 stimulated interferon gamma (IFNγ) was measured in human peripheral blood mononuclear cells (PBMCs) isolated from human whole blood (Stanford Blood Center). Because IL-2 signals through JAK, this assay provides a measure of JAK cellular potency.

(1) Human peripheral blood mononuclear cells (PBMC) were isolated from human whole blood of healthy donors using a ficoll gradient. Cells were cultured in a 37° C., 5% $CO_2$ humidified incubator in RPMI (Life Technologies) supplemented with 10% Heat Inactivated Fetal Bovine Serum (FBS, Life Technologies), 2 mM Glutamax (Life Technologies), 25 mM HEPES (Life Technologies) and 1×Pen/Strep (Life Technologies). Cells were seeded at 200,000 cells/well in media (50 µL) and cultured for 1 h. Compounds were serially diluted in DMSO and then diluted another 500-fold (to a 2× final assay concentration) in media. Test compounds (100 µL/well) were added to cells, and incubated at 37° C., 5% $CO_2$ for 1 h, followed by the addition of IL-2 (R&D Systems; final concentration 100 ng/mL) and anti-CD3 (BD Biosciences; final concentration 1 µg/mL) in pre-warmed assay media (50 µL) for 24 h.

(2) After cytokine stimulation, cells were centrifuged at 500 g for 5 min and supernatants removed and frozen at −80° C. To determine the inhibitory potency of the test compound in response to IL-2/anti-CD3, supernatant IFNγ concentrations were measured via ELISA (R&D Systems). $IC_{50}$ values were determined from analysis of the inhibition curves of concentration of IFNγ vs compound concentration. Data are expressed as $pIC_{50}$ (negative decadic logarithm $IC_{50}$) values. The compound of the invention exhibited a $pIC_{50}$ value of about 7.3 in this assay.

Assay 4: Cellular JAK Potency Assay: Inhibition of IL-2 Stimulated pSTAT5 in CD4+ T Cells The potency of the test compound for inhibition of interleukin-2 (IL-2)/anti-CD3 stimulated STAT5 phosphorylation was measured in CD4-positive (CD4+) T cells in human peripheral blood mononuclear cells (PBMCs) isolated from human whole blood (Stanford Blood Center) using flow cytometry. Because IL-2 signals through JAK, this assay provides a measure of JAK cellular potency.

CD4+ T cells were identified using a phycoerythrobilin (PE) conjugated anti-CD4 antibody (Clone RPA-T4, BD Biosciences), while an Alexa Fluor 647 conjugated anti-pSTAT5 antibody (pY694, Clone 47, BD Biosciences) was used to detect STAT5 phosphorylation.

(1) The protocol of Assay 3 paragraph (1) was followed with the exception that the cytokine stimulation with anti-CD3 was performed for 30 min instead of 24 h.

(2) After cytokine stimulation, cells were fixed with pre warmed fix solution (200 µL; BD Biosciences) for 10 min at 37° C., 5% C02, washed twice with DPBS buffer (1 mL, Life Technologies), and resuspended in ice cold Perm Buffer III (1000 µL, BD Biosciences) for 30 min at 4° C. Cells were washed twice with 2% FBS in DPBS (FACS buffer), and then resuspended in FACS buffer (100 µL) containing anti-CD4 PE (1:50 dilution) and anti-CD3 anti-CD3Alexa Fluor 647 (1:5 dilution) for 60 min at room temperature in the dark. After incubation, cells were washed twice in FACS buffer before being analyzed using a LSRII flow cytometer (BD Biosciences). To determine the inhibitory potency of test compounds in response to IL-2/anti-CD3, the median fluorescent intensity (MFI) of pSTAT5 was measured in CD4+ T cells. $IC_{50}$ values were determined from analysis of the inhibition curves of MFI vs compound concentration. Data are expressed as $pIC_{50}$ (negative decadic logarithm $IC_{50}$) values. The compound of the invention exhibited a $pIC_{50}$ value of about 7.7 in this assay.

Assay 5: Cellular JAK Potency Assay: Inhibition of IL-4 Stimulated pSTAT6 in CD3+ T Cells The potency of the test compound for inhibition of interleukin-4 (IL-4) stimulated STAT6 phosphorylation was measured in CD3-positive (CD3+) T cells in human peripheral blood mononuclear cells (PBMCs) isolated from human whole blood (Stanford Blood Center) using flow cytometry. Because IL-4 signals through JAK, this assay provides a measure of JAK cellular potency.

CD3+ T cells were identified using a phycoerythrobilin (PE) conjugated anti-CD3 antibody (Clone UCHT1, BD Biosciences), while an Alexa Fluor 647 conjugated anti-pSTAT6 antibody (pY641, Clone 18/P, BD Biosciences) was used to detect STAT6 phosphorylation.

Human peripheral blood mononuclear cells (PBMC) were isolated from human whole blood of healthy donors as in Assays 3 and 4. Cells were seeded at 250,000 cells/well in media (200 µL), cultured for 1 h and then resuspended in assay media (50 µL) (RPMI supplemented with 0.1% bovine serum albumin (Sigma), 2 mM Glutamax, 25 mM HEPES and 1×Penstrep) containing various concentrations of test compounds. Compounds were serially diluted in DMSO and then diluted another 500-fold (to a 2× final assay concentration) in assay media. Test compounds (50 µL) were incubated with cells at 37° C., 5% $CO_2$ for 1 h, followed by the addition of IL-4 (50 µL) (R&D Systems; final concentration 20 ng/mL) in pre-warmed assay media for 30 min. After cytokine stimulation, cells were fixed with pre-warmed fix solution (100 µL) (BD Biosciences) for 10 min at 37° C., 5% $CO_2$, washed twice with FACS buffer (1 mL) (2% FBS in DPBS), and resuspended in ice cold Perm Buffer III (1000 µL) (BD Biosciences) for 30 min at 4° C. Cells were washed twice with FACS buffer, and then resuspended in FACS buffer (100 µL) containing anti-CD3 PE (1:50 dilution) and anti-pSTAT6 Alexa Fluor 647 (1:5 dilution) for 60 min at room temperature in the dark. After incubation, cells were washed twice in FACS buffer before being analyzed using a LSRII flow cytometer (BD Biosciences).

To determine the inhibitory potency of the test compound in response to IL-4, the median fluorescent intensity (MFI) of pSTAT6 was measured in CD3+ T cells. $IC_{50}$ values were determined from analysis of the inhibition curves of MFI vs compound concentration. Data are expressed as $pIC_{50}$ (negative decadic logarithm $IC_{50}$). The compound of the invention exhibited a $pIC_{50}$ value of 8.1 in this assay.

Assay 6: Cellular JAK Potency Assay: Inhibition of IL-6 Stimulated pSTAT3 in CD3+ T Cells A protocol analogous to that of Assay 5 was used to determine the potency of the test compound for inhibition of interleukin-6 (IL-6) stimulated STAT3 phosphorylation. An Alexa Fluor 647 conjugated anti-pSTAT3 antibody (pY705, Clone 4/P, BD Biosciences) was used to detect STAT3 phosphorylation.

The compound of the invention exhibited a $pIC_{50}$ value of 7.4 in this assay.

Assay 7: Cellular JAK Potency Assay: Inhibition of IFNγ-Induced pSTAT1

The potency of the test compound for inhibition of interferon gamma (IFNγ) stimulated STAT1 phosphorylation was measured in CD14-positive (CD14+) monocytes derived from human whole blood (Stanford Blood Center) using flow cytometry. Because IFNγ signals through JAK, this assay provides a measure of JAK cellular potency.

Monocytes were identified using a fluorescein isothiocyanate (FITC) conjugated anti-CD14 antibody (Clone RM052, Beckman Coulter), and an Alexa Fluor 647 conjugated anti-pSTAT1 antibody (pY701, Clone 4a, BD Biosciences) was used to detect STAT1 phosphorylation.

Human peripheral blood mononuclear cells (PBMC) were isolated from human whole blood of healthy donors using a ficoll gradient. Cells were cultured in a 37° C., 5% $CO_2$ humidified incubator in RPMI (Life Technologies) supplemented with 10% Fetal Bovine Serum (FBS, Life Technologies), 2 mM Glutamax (Life Technologies), 25 mM HEPES (Life Technologies) and 1×Pen/Strep (Life Technologies). Cells were seeded at 250,000 cells/well in media (200 μL), cultured for 2 h and resuspended in assay media (50 μL) (RPMI supplemented with 0.1% bovine serum albumin (Sigma), 2 mM Glutamax, 25 mM HEPES and 1×Penstrep) containing various concentrations of test compounds. The compound was serially diluted in DMSO and then diluted another 1000-fold in media to bring the final DMSO concentration to 0.1%. Test compound dilutions were incubated with cells at 37° C., 5% $CO_2$ for 1 h, followed by the addition of pre-warmed IFNγ (R&D Systems) in media (50 μL) at a final concentration of 0.6 ng/mL for 30 min. After cytokine stimulation, cells were fixed with pre-warmed fix solution (100 μL) (BD Biosciences) for 10 min at 37° C., 5% $CO_2$, washed twice with FACS buffer (1 mL) (1% BSA in PBS), resuspended in 1:10 anti-CD14 FITC:FACS buffer (100 μL), and incubated at 4° C. for 15 min. Cells were washed once, and then resuspended in ice cold Perm Buffer III (BD Biosciences) (100 μL) for 30 min at 4° C. Cells were washed twice with FACS buffer, and then resuspended in 1:10 anti-pSTAT1 Alexa Fluor 647:FACS buffer (100 μL) for 30 min at RT in the dark, washed twice in FACS buffer, and analyzed using a LSRII flow cytometer (BD Biosciences).

To determine the inhibitory potency of the test compound, the median fluorescent intensity (MFI) of pSTAT1 was measured in CD14+ monocytes. $IC_{50}$ values were determined from analysis of the inhibition curves of MFI vs compound concentration. Data are expressed as $pIC_{50}$ (negative decadic logarithm $IC_{50}$) values The compound of the invention exhibited a $pIC_{50}$ value of about 7.5 in this assay.

Assay 8: Ocular Pharmacokinetics in Rabbit Eyes

The objective of this assay was to determine the pharmacokinetics of the test compound in rabbit ocular tissues.

Solution Formulation

The compound of the invention, 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol (1) was dissolved in either 10% 2-hydroxypropyl-β-cyclodextrin to attain a target concentration of 4 mg/mL or in purified water to attain a target concentration of 1 mg/mL. Bilateral intravitreal injection (50 μL/eye) of the solution of test compound was administered to New Zealand white rabbits in two dose groups, 200 μg/eye and 50 μg/eye, respectively, for the cyclodextrin and water vehicle formulations, respectively. The test compound concentration was measured in ocular tissues: vitreous, aqueous, retina/choroid and iris-ciliary body at pre-determined time points post injection (30 min, 4 h, 1 d, 3 d, 7 d, 14 d). Two rabbits (four eyes) were dosed for each time point. In the vitreous tissue, compound 1 exhibited a two-phase decrease in concentration characterized by an initial decrease in concentration with a half-life of approximately 12 hours and finally a terminal half-life of approximately 3.6 days. The compound was found to distribute quickly into the retinal and choroidal region as well and shows a similar pharmacokinetic profile as in the vitreous tissue.

Suspension Formulation

A suspension formulation was prepared by combining crystalline compound 1 of Example 1 with 0.5% hydroxypropyl methylcellulose (HPMC E5)+0.02% Tween 80 to attain a target concentration of 10 mg/mL. Bilateral intravitreal injection (50 μL/eye) of the suspension of test compound was administered to New Zealand white rabbits (500 μg/eye). The test compound concentration was measured in ocular tissues as in the suspension formulation assay at 30 min, 2 wks, 4 wks, 6 wks, and 8 wks post injection. The compound showed a linear decrease in drug concentration in the vitreous from 30 min to 6 weeks with a clearance rate of approximately 3 μg/mL/day. The behavior is consistent with the solubility of compound 1 in the vehicle and the ocular pharmacokinetic behavior in the solution formulation. The drug concentration in plasma was measured and found to be at least 3 orders of magnitude lower than the concentration in vitreous tissue.

Assay 9: Pharmacodynamic Assay: Inhibition of IL6-Induced pSTAT3 in Rats

The ability of a single intravitreal administration of test compound to inhibit IL-6 induced pSTAT3 was measured in rat retina/choroid homogenates.

Suspension formulations were prepared by combining crystalline compound 1 of Example 1 with 0.5% hydroxypropyl methylcellulose (HPMC E5 LV), 0.02% Tween 80, and 0.9% sodium chloride in purified water to attain target concentrations of 3 mg/mL and 10 mg/mL.

Female Lewis rats were intravitreally (IVT) dosed (5 μL per eye) with the suspension formulations or with the drug vehicle. Three days later, IL-6 (Peprotech; 0.1 mg/mL; 5 μL per eye) or vehicle was intravitreally administered to induce pSTAT3. Ocular tissues were dissected one hour after the second IVT injection with IL-6. The retina/choroid tissues were homogenized and pSTAT3 levels were measured using an ELISA (Cell Signaling Technology). The percent inhibition of IL-6-induced pSTAT3 was calculated in comparison to the vehicle/vehicle and vehicle/IL-6 groups. Inhibition of greater than 100% reflects a reduction of pSTAT3 levels to below those observed in the vehicle/vehicle group.

With a 3 day pre-treatment prior to IL-6 challenge, the 15 μg dose and the 50 μg dose of the compound of the invention administered by the suspension formulation inhibited IL-6-induced pSTAT3 by 33% and 109%, respectively in the retina/choroid tissues.

Assay 10: Pharmacodynamic Assay: Inhibition of IFNγ-Induced IP-10 in Rabbits

The ability of a single intravitreal administration of test compound to inhibit interferon-gamma (IFNγ) induced IP-10 protein levels was measured in rabbit vitreous and retina/choroid tissues.

Solution formulations at concentrations of 1 mg/mL and 4 mg/mL of compound 1 of Example 1 were prepared as in Assay 8. A suspension formulation was prepared by combining crystalline compound 1 of Example 1 with 0.5% hydroxypropyl methylcellulose (HPMC E5), 0.02% Tween 80, and 9 mg/mL sodium chloride in purified water to attain a target concentration of 20 mg/mL.

Male, New Zealand White rabbits (Liveon Biolabs, India) were used for the studies. Animals were acclimated after arrival at the research facilities (Jubilant Biosys Ltd., India). Each rabbit was given a total of two intravitreal (IVT) injections with a total dose volume of 50 μL per eye. The first IVT injection (45 μL per eye) delivered test compound or vehicle at a prescribed time point (i.e. 24 hours for the solution formulations or 1 week for the suspension formulation). The second IVT injection (5 μL per eye) delivered IFNγ (1 μg/eye; Stock solution 1 mg/mL; Kingfisher Biotech) or vehicle for the induction of IP-10. In brief, on the day of the injections, rabbits were anesthetized with an intramuscular injection of ketamine (35 mg/kg) and xylazine (5 mg/kg). Once deeply anesthetized, each eye was rinsed with sterile saline and IVT injections were performed using a 0.5 mL insulin syringe (50 units=0.5 mL) with a 31-gauge needle at the supra-nasal side of the both eyes by marking the position with a Braunstein fixed caliper (2¾") 3.5 mm from the rectus muscle and 4 mm from the limbus.

Tissues were collected 24 hours after the second IVT injection with IFNγ. Vitreous humor (VH) and retina/choroid tissues (R/C) were collected and homogenized, and IP-10 protein levels were measured using a rabbit CXCL10 (IP-10) ELISA kit (Kingfisher Biotech). The percent inhibition of IFNγ-induced IP-10 was calculated in comparison to the vehicle/vehicle and vehicle/IFNγ groups.

When dosed as a solution, with a 24 hour pre-treatment prior to the IFNγ challenge, 45 μg of compound 1 inhibited IFNγ-induced IP-10 by 70% and 86/o in the vitreous humor and retina/choroid tissue, respectively, while 180 μg of the compound inhibited IFNγ-induced IP-10 by 91% and 100% in the vitreous humor and retina/choroid tissue, respectively.

With a 1 week pre-treatment prior to the IFNγ challenge, the crystalline suspension formulation of compound 1 inhibited IFNγ-induced IP-10 by 100% in both the vitreous humor and retina/choroid tissues.

Assay 11: Pharmacokinetics in Plasma and Lung in Mouse

Plasma and lung levels of the test compound and the ratio thereof was determined in the following manner. BALB/c mice from Charles River Laboratories were used in the assay. Test compounds were individually formulated in 20% propylene glycol in pH 4 citrate buffer at a concentration of 0.2 mg/mL and 50 uL of the dosing solution was introduced into the trachea of a mouse by oral aspiration. At various time points (typically 0.167, 2, 6, 24 hr) post dosing, blood samples were removed via cardiac puncture and intact lungs were excised from the mice. Blood samples were centrifuged (Eppendorf centrifuge, 5804R) for 4 minutes at approximately 12,000 rpm at 4° C. to collect plasma. Lungs were padded dry, weighed, and homogenized at a dilution of 1:3 in sterile water. Plasma and lung levels of test compound were determined by LC-MS analysis against analytical standards constructed into a standard curve in the test matrix. A lung to plasma ratio was determined as the ratio of the lung AUC in μg hr/g to the plasma AUC in μg hr/mL, where AUC is conventionally defined as the area under the curve of test compound concentration vs. time.

The compound of the invention exhibited exposure in lung about 55 times greater than exposure in plasma in mouse.

Assay 12: Murine (Mouse) Model of IL-13 Induced pSTAT6 Induction in Lung Tissue

Il-13 is an important cytokine underlying the pathophysiology of asthma (Kudlacz et al. *Eur. J. Pharmacol*, 2008, 582, 154-161). IL-13 binds to cell surface receptors activating members of the Janus family of kinases (JAK) which then phosphorylate STAT6 and subsequently activates further transcription pathways. In the described model, a dose of IL-13 was delivered locally into the lungs of mice to induce the phosphorylation of STAT6 (pSTAT6) which is then measured as the endpoint.

Adult balb/c mice from Harlan were used in the assay. On the day of study, animals were lightly anesthetized with isoflurane and administered either vehicle or test compound (0.5 mg/mL, 50 μL total volume over several breaths) via oral aspiration. Animals were placed in lateral recumbency post dose and monitored for full recovery from anesthesia before being returned to their home cage. Four hours later, animals were once again briefly anesthetized and challenged with either vehicle or IL-13 (0.03 μg total dose delivered, 50 μL total volume) via oral aspiration before being monitored for recovery from anesthesia and returned to their home cage. One hour after vehicle or IL-13 administration, lungs were collected for both pSTAT6 detection using an anti-pSTAT6 ELISA (rabbit mAb capture/coating antibody; mouse mAb detection/report antibody: anti-pSTAT6-pY641; secondary antibody: anti-mouse IgG-HRP) and analyzed for total drug concentration as described above in Assay 11.

Activity in the model is evidenced by a decrease in the level of pSTAT6 present in the lungs of treated animals at 5 hours compared to the vehicle treated, IL-13 challenged control animals. The difference between the control animals which were vehicle-treated, IL-13 challenged and the control animals which were vehicle-treated, vehicle challenged dictated the 0% and 100% inhibitory effect, respectively, in any given experiment. The compound of the invention exhibited about 60% inhibition of STAT6 phosphorylation at 4 hours after IL-13 challenge.

Assay 13: Murine Model of *Alternaria alternata*-Induced Eosinophilic Inflammation of the Lung Airway eosinophilia is a hallmark of human asthma. *Alternaria alternata* is a fungal aeroallergen that can exacerbate asthma in humans and induces eosinophilic inflammation in the lungs of mice (Havaux et al. *Clin Exp Immunol.* 2005, 139(2):179-88). In mice, it has been demonstrated that *alternaria* indirectly activates tissue resident type 2 innate lymphoid cells in the lung, which respond to (e.g. IL-2 and IL-7) and release JAK-dependent cytokines (e.g. IL-5 and IL-13) and coordinate eosinophilic inflammation (Bartemes et al. *J Immunol.* 2012, 188(3):1503-13).

Seven- to nine-week old male C57 mice from Taconic were used in the study. On the day of study, animals were lightly anesthetized with isoflurane and administered either vehicle or test compound (0.1-1.0 mg/mL, 50 µL total volume over several breaths) via oropharyngeal aspiration. Animals were placed in lateral recumbency post dose and monitored for full recovery from anesthesia before being returned to their home cage. One hour later, animals were once again briefly anesthetized and challenged with either vehicle or *alternaria* extract (200 ug total extract delivered, 50 µL total volume) via oropharyngeal aspiration before being monitored for recovery from anesthesia and returned to their home cage. Forty-eight hours after *alternaria* administration, bronchoalveolar lavage fluid (BALF) was collected and eosinophils were counted in the BALF using the Advia 120 Hematology System (Siemens).

Activity in the model is evidenced by a decrease in the level of eosinophils present in the BALF of treated animals at forty-eight hours compared to the vehicle treated, *alternaria* challenged control animals. Data are expressed as percent inhibition of the vehicle treated, *alternaria* challenged BALF eosinophils response. To calculate percent inhibition, the number of BALF eosinophils for each condition is converted to percent of the average vehicle treated, *alternaria* challenged BALF eosinophils and subtracted from one-hundred percent. The compound of the invention exhibited about 88% inhibition of BALF eosinophil counts at forty-eight hours after *alternaria* challenge.

Assay 14: Murine Model of LPS/G-CSF/IL-6/IFNγ Cocktail-Induced Airway Neutrophilic Inflammation of the Lung Model Airway neutrophilia is a hallmark of a range of respiratory disease in humans. Compound 1 was tested in a model of neutrophilic airway inflammation using a LPS/G-CSF/IL-6/IFNγ cocktail to induce airway neutrophilia.

Seven- to nine-week old male Balb/C (wildtype) mice from Jackson Laboratory were used in the study. On the day of study, animals were lightly anesthetized with isoflurane and administered either vehicle or test compound (1.0 mg/mL, 50 µL total volume over several breaths) via oropharyngeal aspiration. Animals were placed in lateral recumbency post dose and monitored for full recovery from anesthesia before being returned to their home cage. One hour later, animals were once again briefly anesthetized and challenged with either vehicle or LPS; 0.01 mg/kg/G-CSF; 5 µg/IL-6; 5 µg/IFNγ; 5 µg (100 µL total volume) via oropharyngeal aspiration (OA). Twenty-four hours after the LPS/G-CSF/IL-6/IFNγ cocktail administration, bronchoalveolar lavage fluid (BALF) was collected and neutrophils were counted.

Upon OA treatment with compound 1, there was a statistically significant reduction of the airway neutrophils (84% compared to vehicle treated mice), demonstrating that the blockade of JAK-dependent signaling has effects on neutrophilic airway inflammation.

Assay 15: Inhibition of IFNγ and IL-27 Induced Chemokines CXCL9 and CXCL10 in Human 3D Airway Cultures EpiAirway tissue cultures were obtained from Mattek (AIR-100). Cultures were derived from asthmatic donors. In a cell culture insert, human derived tracheal/bronchial epithelial cells were grown and differentiated on a porous membrane support, allowing an air-liquid interface with warmed culture medium below the cells and a gaseous test atmosphere above. Tissues were cultured in maintenance media (Mattek, AIR-100-MM) in a 37° C., 5% CO2 humidified incubator. Four donors were tested. On Day 0, tissue cultures were treated with test compounds at 10 µM, 1 µM and/or 0.1 µM. Compounds were diluted in dimethyl sulfoxide (DMSO, Sigma) to a final concentration of 0.1%. DMSO at 0.1% was used as a vehicle control. Test compounds were incubated with cultures for 1 hour at 37° C., 5% $CO_2$, followed by the addition of pre-warmed media containing IFNγ (R&D Systems) or IL-27 (R&D Systems) at a final concentration at 100 ng/ml. Tissue cultures were maintained for 8 days. Media was replaced every 2 days with fresh media containing compounds and IFNγ or IL-27. On Day 8, tissue cultures and supernatants were collected for analysis. Supernatant samples were assayed for CXCL10 (IP-10) and CXCL9 (MIG) using luminex analysis (EMD Millipore). Data is expressed as % Inhibition+/−standard deviation (±STDV). Percent inhibition was determined by compound inhibitory potency against IFNγ or IL-27 induced CXCL10 or CXCL9 secretion compared to vehicle treated cells. Data is the average from 3 or 4 donors. Compound 1 was able to inhibit IFNγ induced CXCL10 secretion by 99%±2.0 (at 10 µM), 71%±19 (at µM) and 17%±12 (at 0.1 µM) when compared to vehicle control. Compound 1 was able to inhibit IFNγ induced CXCL9 secretion by 100%±0.3 (at 10 µM), 99%±0.9 (at 1 µM) and 74%±17 (at 0.1 µM) when compared to vehicle. Compound 1 was able to inhibit IL-27 induced CXCL10 secretion by 108%±11 (at 10 µM), 98%±10 (at 0.1 µM) and 73%±8.5 (at 0.1 µM) when compared to vehicle control. Compound 1 was able to inhibit IL-27 induced CXCL9 secretion by 100%±0 (at 10 µM), 95%±3.7 (at 1 µM) and 75%±3.5 (at 0.1 µM) when compared to vehicle control.

Assay 16: IL-5 Mediated Eosinophil Survival Assay

The potency of the test compound for IL-5 mediated eosinophil survival was measured in human eosinophils isolated from human whole blood (AllCells). Because IL-5 signals through JAK, this assay provides a measure of JAK cellular potency.

Human eosinophils were isolated from fresh human whole blood (AllCells) of healthy donors. Blood was mixed with 4.5% Dextran (Sigma-Aldrich) in a 0.9% sodium chloride solution (Sigma-Aldrich). Red blood cells were left to sediment for 35 minutes. The leukocyte rich upper layer was removed and layered over Ficoll-Paque (GE Healthcare) and centrifuged at 600 g for 30 minutes. The plasma and mononuclear cell layers were removed before the granulocyte layer was lysed with water to remove any contaminating red blood cells. Eosinophils were further purified using a human eosinophil isolation kit (Miltenyi Biotec). A fraction of the purified eosinophils were incubated with anti-CD16 FITC (Miltenyi Biotec) for 10 minutes at 4° C. in the dark. Purity was analyzed using a LSRII flow cytometer (BD Biosciences).

Cells were cultured in a 37° C., 5% $CO_2$ humidified incubator in RPMI 1640 (Life Technologies) supplemented with 10% Heat Inactivated Fetal Bovine Serum (FBS, Life Technologies), 2 mM Glutamax (Life Technologies), 25 mM HEPES (Life Technologies) and 1×Pen/Strep (Life Technologies). Cells were seeded at 10,000 cells/well in media (50 µL). The plate was centrifuged at 300 g for 5 minutes and supernatants removed. Compounds were serially diluted in DMSO and then diluted another 500-fold to a 2× final assay concentration in media. Test compounds (50 µL/well) were added to cells, and incubated at 37° C., 5% $CO_2$ for 1 hour, followed by the addition of IL-5 (R&D Systems; final concentrations 1 ng/mL and 10 µg/ml) in pre-warmed assay media (50 µL) for 72 hours.

After cytokine stimulation, cells were centrifuged at 300 g for 5 min and washed twice with cold DPBS (Life Technologies). To access viability and apoptosis, cells were incubated with Propidium Iodide (Thermo Fisher Scientific) and APC Annexin V (BD Biosciences) and analyzed using a LSRII flow cytometer (BD Biosciences). $IC_{50}$ values were determined from analysis of the viability curves of percent cell viability vs compound concentration. Data are expressed as $pIC_{50}$ (negative decadic logarithm $IC_{50}$) values. Compound 1 exhibited a $pIC_{50}$ value of 7.9±0.5 in the presence of 10 μg/ml IL-5 and a $pIC_{50}$ value of 6.5±0.2 in the presence of 1 ng/ml IL-5.

Assay 17: Pharmacodynamic Assay: Inhibition of IFNγ-Induced pSTAT1 in Rabbit Eyes The ability of a single intravitreal administration of test compound to inhibit interferon-gamma (IFNγ) induced phosphorylation of STAT1 protein (pSTAT1) was measured in rabbit retina/choroid tissue.

A suspension formulation was prepared by combining compound 1 of Example 1, with 0.5% hydroxypropyl methylcellulose (HPMC E5), 0.02% Tween 80, and 9 mg/mL sodium chloride in purified water to attain a target concentration of 20 mg/mL.

Male, New Zealand White rabbits (Liveon Biolabs, India) were used for the studies. Animals were acclimated after arrival at the research facilities (Jubilant Biosys Ltd., India). Each rabbit was given a total of two intravitreal (IVT) injections with a total dose volume of 50 μL per eye. The first IVT injection (45 μL per eye) delivered 0.9 mg of test compound or vehicle. One week later, a second IVT injection (5 μL per eye) delivered IFNγ (1 μg/eye; stock solution 1 mg/mL; Kingfisher Biotech) or vehicle for the induction of IP-10. On the day of the injections, rabbits were anesthetized with an intramuscular injection of ketamine (35 mg/kg) and xylazine (5 mg/kg). Once deeply anesthetized, each eye was rinsed with sterile saline and IVT injections were performed using a 0.5 mL insulin syringe (50 units=0.5 mL) with a 31-gauge needle at the supra-nasal side of the both eyes by marking the position with a Braunstein fixed caliper (2¾") 3.5 mm from the rectus muscle and 4 mm from the limbus.

Tissues were collected 2 hours after the second IVT injection with IFNγ. Retina/choroid tissues (R/C) were collected and homogenized, and pSTAT1 levels were measured by quantitative Western Blot on the ProteinSimple WES instrument. The percent inhibition of IFNγ-induced pSTAT1 was calculated in comparison to the vehicle/vehicle and vehicle/IFNγ groups.

With a 1 week pre-treatment prior to the IFNγ challenge, the suspension formulation of compound 1 of Example 1 inhibited IFNγ-induced pSTAT1 by 85%.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:

1. A method of treating sarcoidosis in a human, the method comprising administering to the human a pharmaceutical composition comprising 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol, or a pharmaceutically acceptable salt thereof, and a pharmaceutically-acceptable carrier.

2. The method of claim 1 wherein the pharmaceutical composition is administered by inhalation.

3. The method of claim 2 wherein the pharmaceutical composition is administered by a nebulizer inhaler.

4. The method of claim 2 wherein the pharmaceutical composition is administered by a dry powder inhaler.

5. The method of claim 1, wherein the pharmaceutical composition is a solution.

6. The method of claim 1, wherein the pharmaceutical composition is a suspension.

7. The method of claim 1, wherein the pharmaceutical composition is a dry powder.

8. The method of claim 1, wherein 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol is in the form of a free base.

9. The method of claim 1, wherein 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol is in the form of a pharmaceutically acceptable salt.

10. The method of claim 1, wherein 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol is in the form of a crystalline hydrate.

11. The method of claim 10, wherein the crystalline hydrate is characterized by a powder X-ray diffraction pattern comprising diffraction peaks at 2θ values of 6.20±0.20, 9.58±0.20, 17.53±0.20, 19.28±0.20, and 21.51±0.2.

12. The method of claim 11, wherein the powder X-ray diffraction pattern is further characterized by having two or more additional diffraction peaks at 2θ values selected from 10.34±0.20, 11.54±0.20, 12.77±0.20, 13.01±0.20, 16.94±0.20, 20.61±0.20, and 22.10±0.20.

13. A method of treating sarcoidosis in a mammal, the method comprising administering to the mammal the compound 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol, or a pharmaceutically acceptable salt thereof.

14. The method of claim 13, wherein the mammal is a human.

15. The method of claim 14, wherein the compound is administered by inhalation.

16. The method of claim 14, wherein the compound is administered by a nebulizer inhaler.

17. The method of claim 14 wherein the compound is administered by a dry powder inhaler.

18. The method of claim 14, wherein the compound is administered as a free base.

19. The method of claim 14, wherein the compound is administered as a pharmaceutically acceptable salt.

20. The method of claim 14, wherein the compound is administered as a crystalline hydrate.

* * * * *